(12) United States Patent
Ramachandran et al.

(10) Patent No.: US 9,289,481 B2
(45) Date of Patent: Mar. 22, 2016

(54) INCAPACITATED WHOLE-CELL IMMUNOGENIC BACTERIAL COMPOSITIONS PRODUCED BY RECOMBINANT EXPRESSION

(75) Inventors: Janakiraman Ramachandran, Palo Alto, CA (US); Sriram Padmanabhan, Sanjaynagar (IN); Bharathi Sriram, Sanjaynagar (IN)

(73) Assignee: Gangagen, Inc., Newark, CA (US)

( * ) Notice: Subject to any disclaimer, the term of this patent is extended or adjusted under 35 U.S.C. 154(b) by 40 days.

(21) Appl. No.: 12/560,321

(22) Filed: Sep. 15, 2009

(65) Prior Publication Data

US 2010/0303862 A1    Dec. 2, 2010

Related U.S. Application Data

(63) Continuation of application No. 10/715,348, filed on Nov. 14, 2003, now abandoned.

(60) Provisional application No. 60/426,670, filed on Nov. 14, 2002.

(51) Int. Cl.

| A61K 39/02 | (2006.01) |
|---|---|
| A61P 37/04 | (2006.01) |
| C12N 15/74 | (2006.01) |
| A61K 39/108 | (2006.01) |
| A61K 39/00 | (2006.01) |

(52) U.S. Cl.
CPC ............ *A61K 39/02* (2013.01); *A61K 39/0258* (2013.01); *A61K 2039/522* (2013.01)

(58) Field of Classification Search
USPC ....................................... 424/234.1; 435/471
See application file for complete search history.

(56) References Cited

U.S. PATENT DOCUMENTS

| 4,376,110 A | 3/1983 | David et al. |
|---|---|---|
| 6,056,955 A | 5/2000 | Fischetti et al. |
| 6,083,684 A | 7/2000 | Gasson |
| 6,130,082 A | 10/2000 | Majararian et al. |
| 6,395,504 B1 | 5/2002 | Trudil |
| 6,605,286 B2 * | 8/2003 | Steidler et al. ............. 424/243.1 |
| 6,773,899 B2 | 8/2004 | Kordyum et al. |
| 2003/0118558 A1 | 6/2003 | Ramachandran et al. |
| 2003/0152589 A1 | 8/2003 | Ramachandran et al. |

OTHER PUBLICATIONS

Abul-Hassan, et al., *Annals of the MBC*, vol. 3(4), pp. 1-4 (1990).
Ackermann, *Adv. Virus Res.*, vol. 51, pp. 135-201 (1998).
Amann et al. *Gene*, vol. 25, pp. 167-1782 (1983).
Amann et al. *Gene*, vol. 69, pp. 301-315 (1988).
Arendt, et al., *Applied and Environment Microbiology*, vol. 6(6), pp. 1875-1883 (Jun. 1994).
Auad, et al., *Arch Virol.*, vol. 144, pp. 1503-1512 (1999).
Barrow, et al., *Clinical and Diagnostic Laboratory Immunology*, vol. 5(3), pp. 294-298 (May 1998).
Bernhardt, et al., *Proc. Natl. Acad. Sci.*, vol. 97(8), pp. 4297-4302 (Apr. 2000).
Biswas, et al., *Infection and Immunity*, vol. 70(1), pp. 204-210 (Jan. 2002).
Bloemberg et al., *Appl. Environ. Microbiol.*, pp. 4443-45514 (1997).
Boizet, et al., *Gene*, vol. 94, pp. 61-67 (1990).
Botstein, et al., *Science*, vol. 229(4719), pp. 1193-1201 (1985).
Calandra, et al., *Infect. Immun.*, vol. 12, pp. 13-28 (1975).
Calandra, et al., *Infect. Immun.*, vol. 28, pp. 1033-1037 (1980).
Caldentey, et al., *Biochimica et Biophysica Acta*, vol. 1159, pp. 44-50 (1992).
Cattozzo, et al., *Journal of Biotechnology*, vol. 56, pp. 191-203 (1997).
Chalfie, et al., *Science*, vol. 263, pp. 802-805 (1994).
Chamberlin M. et al., Nature (London), vol. 228, p. 227(1970).
Chamberlin et al. *J. Biol. Chem.*, vol. 248, p. 2235 (1973).
Chandry, et al., *Mol. Microbiol.*, vol. 26, pp. 49-64 (1997).
Cohen, et al., *Appl. Microbiol.*, vol. 29, pp. 175-178 (1975).
Cole, et al., *Monoclonal Antibodies and Cancer Therapy*, pp. 77-96 (1985).
Coleman, et al., *Microb Pathog.*, vol. 1, pp. 549-564 (1986).
Coleman, et al., *J. Gen. Mircobiol.*, vol. 135, pp. 1679-1697 (1989).
Cooney, et al., *J. Gen. Microbiol.*, vol. 134, pp. 2179-2188 (1988).
Cormack, et al., *Gene*, vol. 173, pp. 33-38 (1996).
Cort et al. *Acta Veterinaria Scandinavia*, vol. 31, pp. 347-358 (1980).
Cote, et al., *Proc. Natl. Acad. Sci. USA*, vol. 80, pp. 2026-2030 (1983).
Culbertson et al. *Vetenary Scientific Communications*, vol. 4, pp. 3-14 (1980).
Davanloo et al. *Proc. Natl. Acad. Sci*, vol. 81, pp. 2035-2039 (1984).
De Ruyter, et al., *Nat., Biotechnol.*, vol. 15, pp. 976-979 (1997).
Devine, et al., *Chromosome J. Bacteriology*, vol. 129(2), pp. 1072-1077 (1977).
Diaz, et al., *Mol. Microbiol.*, vol. 19, pp. 667-681 (Feb. 1996).
Dietrich, et al., *Nat. Biotechnol.*, vol. 16, pp. 181-185 (1998).
Dunn et al. *J. Mol. Biol.*, vol. 166, p. 477 (1983).
Elias, et al., *Acta Microbiol. Acad. Sci. Hung.*, vol. 27, pp. 183-190 (1980).

(Continued)

*Primary Examiner* — Robert A Zeman
(74) *Attorney, Agent, or Firm* — Kilpatrick Townsend & Stockton LLP

(57) ABSTRACT

The present invention features incapacitated whole-cell bacterial immunogenic compositions and methods of their production, which compositions are useful to deliver antigens in a manner resembling the live infectious organism in terms of elicitation of a robust immune response, but with reduced risk or no risk of disease. The compositions of the invention are produced by rendering a bacterium bacteriostatic through expression of a recombinant promoter in the bacterial cell, which promoter can be operably linked to a polynucleotide encoding a recombinant gene product. In one embodiment, where the bacterium is a gram negative host, the recombinant gene product provides for reduced toxicity of LPS. In one embodiment, the gene product is a bacteriophage protein, such as endolysin, holin, or ndd.

4 Claims, 11 Drawing Sheets

(56) References Cited

OTHER PUBLICATIONS

Fischetti, et al., *J. Exp. Med.*, vol. 133, pp. 1105-1117 (1971).
Gaeng, et al., *Appl., Environ. Microbiol.*, vol. 66, p. 2951 (2000).
Garcia, et al., *J Bacteriol.*, vol. 159(2), pp. 793-796 (Aug. 1984).
Garcia, et al., *J. Virol.*, vol. 61, pp. 2573-2580 (1987).
Garcia, et al., *J. Gen. Microbiol.*, vol. 129, pp. 479-487 (1983).
Garrett, *Mol. Gen. Genet*, vol. 182, p. 326 (1981).
Garvey, et al., *Nucleic Acids Res.*, vol. 14, p. 10001 (1986).
Gindreau, et al., *FEMS Microbiol. Lett*, vol. 171, pp. 231-238 (1999).
Golomb et al. *J. Biol. Chem.*, vol. 249, p. 2858 (1974).
Gründling, et al., *Proc. Nat'l Acad. Sci. USA*, vol. 98(16), pp. 9348-9352 (Jul. 2001).
Gründling, et al., *J. Bacteriol.*, vol. 182(21), pp. 6082-6090 (Nov. 2000).
Guzman et al. *J. Bacteriol.*, vol. 177, pp. 4121-4130 (1992).
Haldimann et al. *J. Bacteriol.* vol. 180, pp. 1277-1286 (1998).
Han et al. *J. Biol. Chem.*, vol. 269(11), pp. 8172-8175 (1994).
Heinkoff, *Gene*, vol. 28, p. 351 (1984).
Henrich, et al., *J. Bacteriol.*, vol. 177, pp. 723-732 (1995).
Higuchi, et al., *Nucleic Acids Res.*, vol. 16, p. 7351 (1988).
Hill, et al., *J. Bacteriol.*, vol. 145, pp. 696-703 (1981).
Hitchcock et al. *J. Bacteriol.*, vol. 166, pp. 699-705 (1986).
Hussaini et al. *Vet. Res. Comm.*, vol. 5, pp. 171-175 (1981).
Ing-Nang Wang et al. *Annu. Rev. Microbiol.*, vol. 54, pp. 799-825 (2000).
Inouye, et al., *Biol. Chem.*, vol. 248, pp. 7247 (1973).
Jain, et al., *Infect. Immun.*, vol. 68, p. 986 (2000).
Jerne, *Ann. Immunol.* (Paris), vol. 125c, pp. 373-389 (1974).
Jerne, et al., *EMBO*, vol. 1, p. 234 (1982).
Kaneko, et al., *Gene*, vol. 215, pp. 57-67 (1998).
Kohler, et al., *Nature*, vol. 256, pp. 495-497 (1975).
Kosbor, et al., *Immunology Today*, vol. 4, p. 72 (1983).
Kuhnemund, Z. *Immunitatsforsch Exp. Klin Immunol.*, vol. 143, pp. 184-191 (1972).
Lee, et al., "Potential of bacteriophage application as an intervention strategy against *Salmonella* in pigs," available on the internet as of 2009 at http://www.ipic.iastate.edu/reports/02swinereports/asl-1810.pdf, 2 pgs.
Loessner, et al., *Mol. Microbiol.* vol. 16, pp. 1231-1241 (Jun. 1995).
Loessner, et al., *Appl. Environ. Microbiol.*, vol. 62, pp. 3057-3060 (1996).
Longchamp, et al., Abstract of the 96th Gen. Meet. of Amer. Soc. For Microbiol., May 19-23, p. 576(Abstract M-16) (1996).
Luria et al. *J. Bacteriol.*, vol. 59, pp. 551-560 (1950).
Martin et al. *J. Bacteriol.*, vol. 180, pp. 210-217 (1998).
Matsuzaki, et al., *J. Infect. Dis.*, vol. 187, pp. 613-624 (2003).
Mermod, et al., *J. Bacteriol.*, vol. 167, p. 447 (1986).
Mindich, et al., *J. Virol.*, vol. 30, pp. 489-496 (1979).
Mullan, et al., *J. Dairy Res.* vol. 52, pp. 113-121 (1985).
Mullan, et al., *J. Dairy Res.*, vol. 52, pp. 123-138 (1985).
Murray et al. *J. Bacteriol.*, vol. 59, pp. 603-615 (1950).
Nelson, et al., *Proc. Natl. Acad. Sci., USA*, vol. 98, pp. 4107-4112 (2001).
Newton, et al., *Res. Microbiol.*, vol. 146, pp. 203-216 (1995).
Newton, et al., *Science*, vol. 244, p. 70 (1989).
Norrby, E., *Summary in Vaccines*, vol. 85, pp. 388-389 (1985).

Oki, et al., *Gene*, vol. 176, pp. 215-223 (1996).
Owen, et al., *J. Mol., Biol.*, vol. 165, p. 229 (1983).
Payne, et al., *FEMS Microbiol. Lett.*, vol. 136, pp. 19-24 (1996).
Raina, *J. Bacteriol.*, vol. 145, pp. 661-663 (1981).
Ramesh, et al., *Anaerobe*, vol. 5, pp. 69-78 (1999).
Rennell, et al., *Virol.*, vol. 143, p. 280 (1985).
Rosenberg, et al., *Ann. Rev. Genet.*, vol. 13, pp. 319-353 (1979).
Sable, et al., *Appl. Microbiol. Biotechnol.*, vol. 43, pp. 1-6 (1995).
Sanders, et al., *Appl. Environ Microbiol.*, vol. 63(12), pp. 4877-4882 (1997).
Schmidt, et al., *J. Bacteriol.*, vol. 178(4), p. 1099-1104 (1996).
Schumann et al. *Science*, vol. 249, p. 1429 (1990).
Shearman, et al., *Mol. Gen. Genet*, vol. 218, pp. 214-221 (1989).
Shearman, et al., *Appl. Environ. Microbiol.*, vol. 60, pp. 3063-3073 (1994).
Sheehan, et al., *FEMS Microbiol. Lett*, vol. 140, pp. 23-28 (1996).
Sheehan, et al., *Mol. Microbiol.* vol. 25, pp. 717-725 (1997).
Sheehan, et al., *Appl. Environ Microbiol.*, vol. 65, pp. 569-577 (1999).
Sherry et al. *J. Cell Biol.*, vol. 107, p. 1269 (1988).
Shortle, et al., *Proc. Natl'l. Acad. Sci. USA*, vol. 79, p. 1588 (1982).
Singer, *Cell*, vol. 31, pp. 25-33 (1982).
Smith, *Ann. Ref. Genet.*, vol. 19, pp. 423-462 (1985).
Smith, et al., *Journal of General Microbiology*, vol. 128, pp. 307-318 (1982).
Smith, *J. Gen. Microbiol.*, vol. 129(pt. 8), pp. 2659-2675 (Aug. 1993).
Smith, *J. Gen. Microbiol.*, vol. 133(pt. 5), pp. 1111-1126 (May 1987).
Sonstein, et al., *J. Bacteriol.* vol. 107, pp. 499-504 (1971).
Spicer, et al., *Bacteriophage* T4 eds., American Society for Microbiology, p. 299 (1983).
Stocker, et al., *Int. Rev. Immunol.* vol. 11, p. 167 (1994).
Stocker, *Res. Microbiol.* vol. 141, pp. 787-796 (1990).
Streisinger, et al., *Symp. Quant. Biol.*, vol. 26, pp. 25-30 (1961).
Studier et al. *J. Mol. Biol.*, vol. 189, pp. 113-130 (1986).
Studier et al. *Methods in Enzymology*, vol. 185, pp. 60-63 (1990).
Tourville, et al., *J. Dairy Sci.*, vol. 49, pp. 158-162 (1966).
Tsugita, et al., *J. Biol. Chem.*, vol. 243, p. 391 (1968).
Vallette, et al., *Nucleic Acids Res.*, vol. 17, p. 723 (1989).
Van Der Vijver, et al., *J. Med. Microbiol.*, vol. 8, pp. 265-277 (1975).
Van Sinderen, et al., *Mol. Microbiol.*, vol. 19, pp. 1343-1355 (1996).
Volker, et al., *Mol. Gen. Genet.*, vol. 177, p. 447 (1980).
Wang, et al., *Ann. Ref. Microbiol.*, vol. 54, pp. 799-825 (2000).
Ward, et al., *Can. J. Microbiol.*, vol. 39, pp. 767-774 (1993).
Wheeler, et al., *J. Gen. Microbiol.*, vol. 120, pp. 27-33 (1980).
Wilson, et al., *Cell*, vol. 37, p. 767 (1984).
Wright et al. *Science*, vol. 249, p. 1431 (1990).
Xu, et al., *Proc. Nat'l Acad. Sci. USA*, vol. 101(17), pp. 6415-6420 (2004).
Yoon, et al., *Int., J. Food Microbiol.*, vol. 65, pp. 63-74 (2001).
Young et al. *Microbiol. Rev.*, vol. 56, pp. 430-481 (1992).
Young et al. *FEMS Micobiol. Rev.*, vol. 17, pp. 191-205 (1995).
Young et al. *Trends Microbiol.*, vol. 8, pp. 120-128 (2000).
Zhao, et al., *Methods Enzymol.*, vol. 217, p. 218 (1993).
Ziermann, et al., *J. Bacteriol.*, vol. 176(16), p. 4974 (1994).
The American Heritage Dictionary of the English Language, 4th Edition, 2000 entry "incapacitated."

* cited by examiner

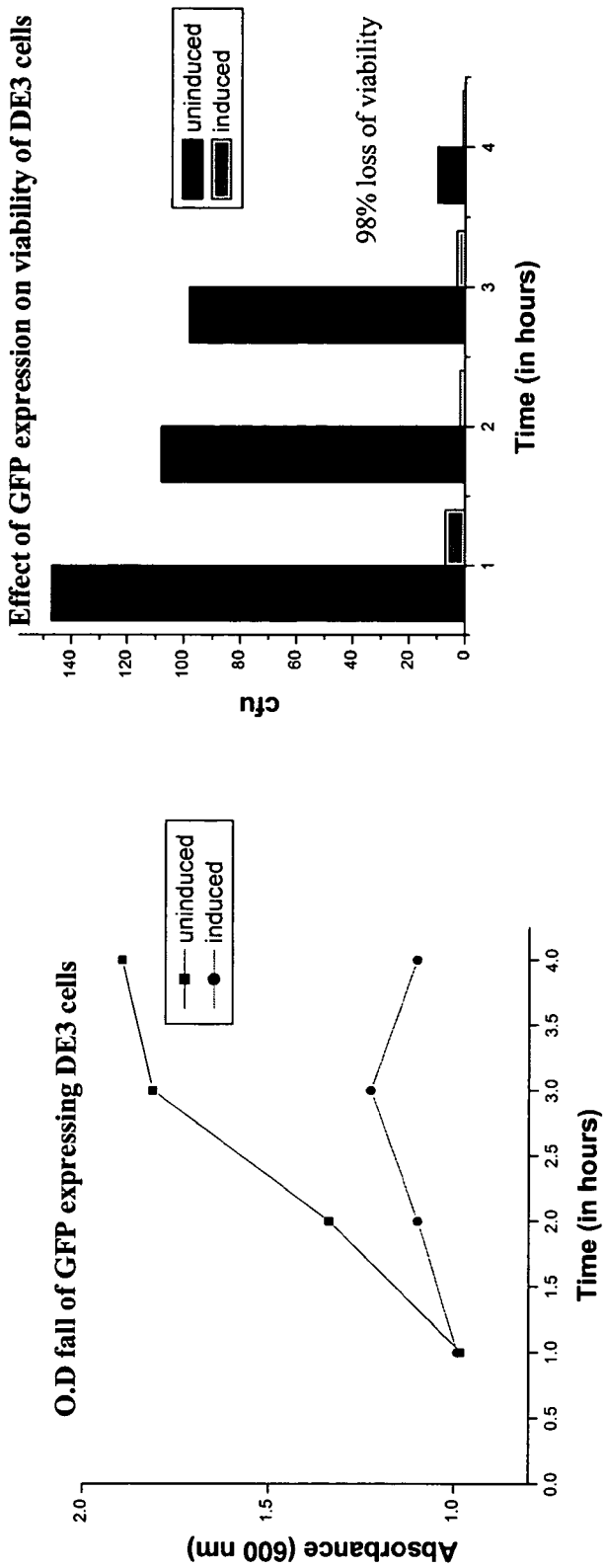
Fig. 1 Effect of rGFP expression on growth and viability of DE3 cells

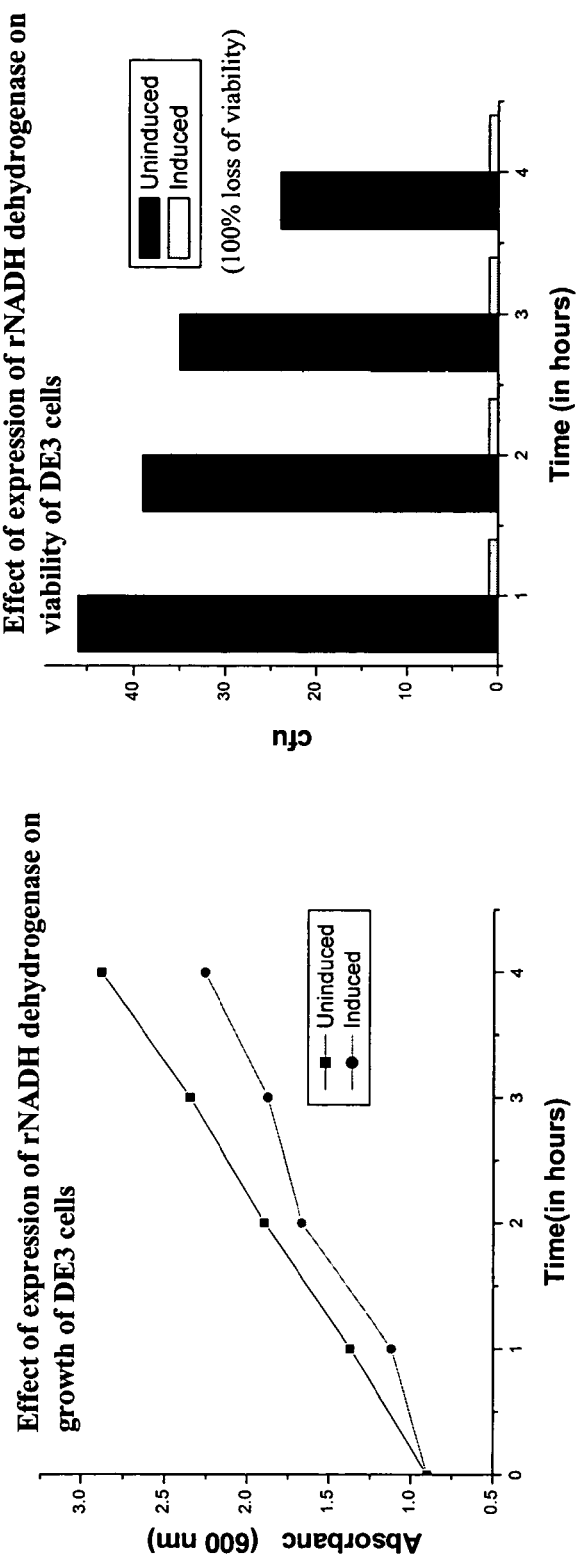
Fig. 2 Effect of expression of rNADH dehydrogenase on growth and viability of DE3 cells

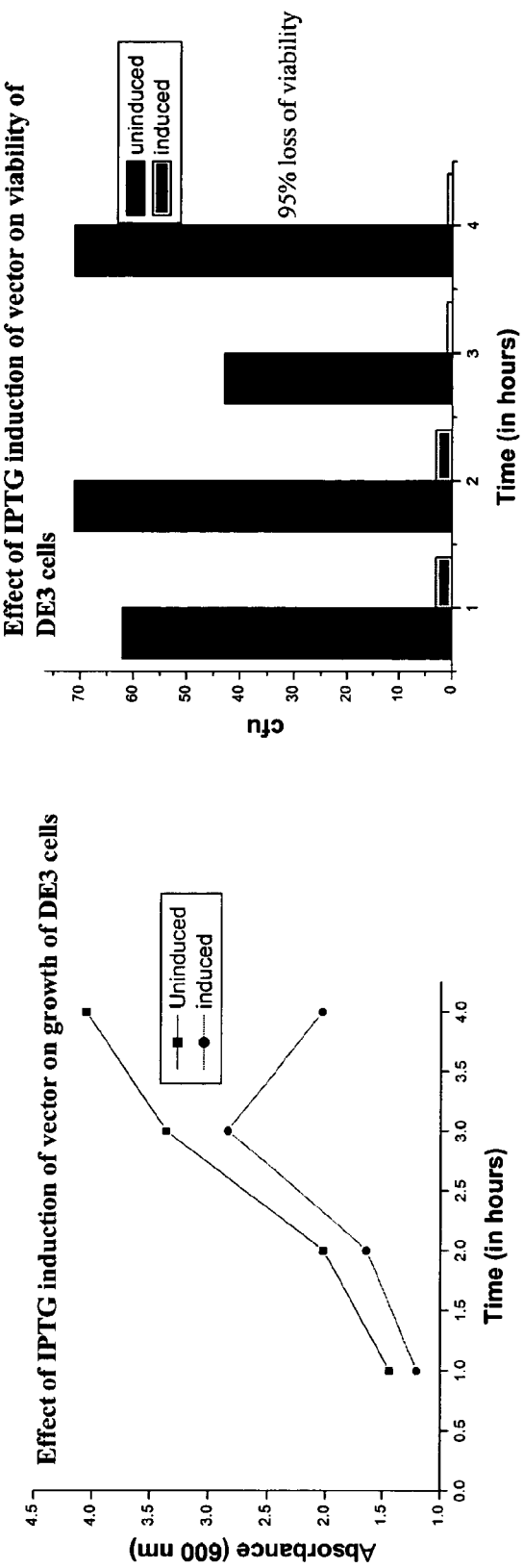
Fig. 3 Effect of IPTG induction of pRSET vector on growth and viability of DE3 cells

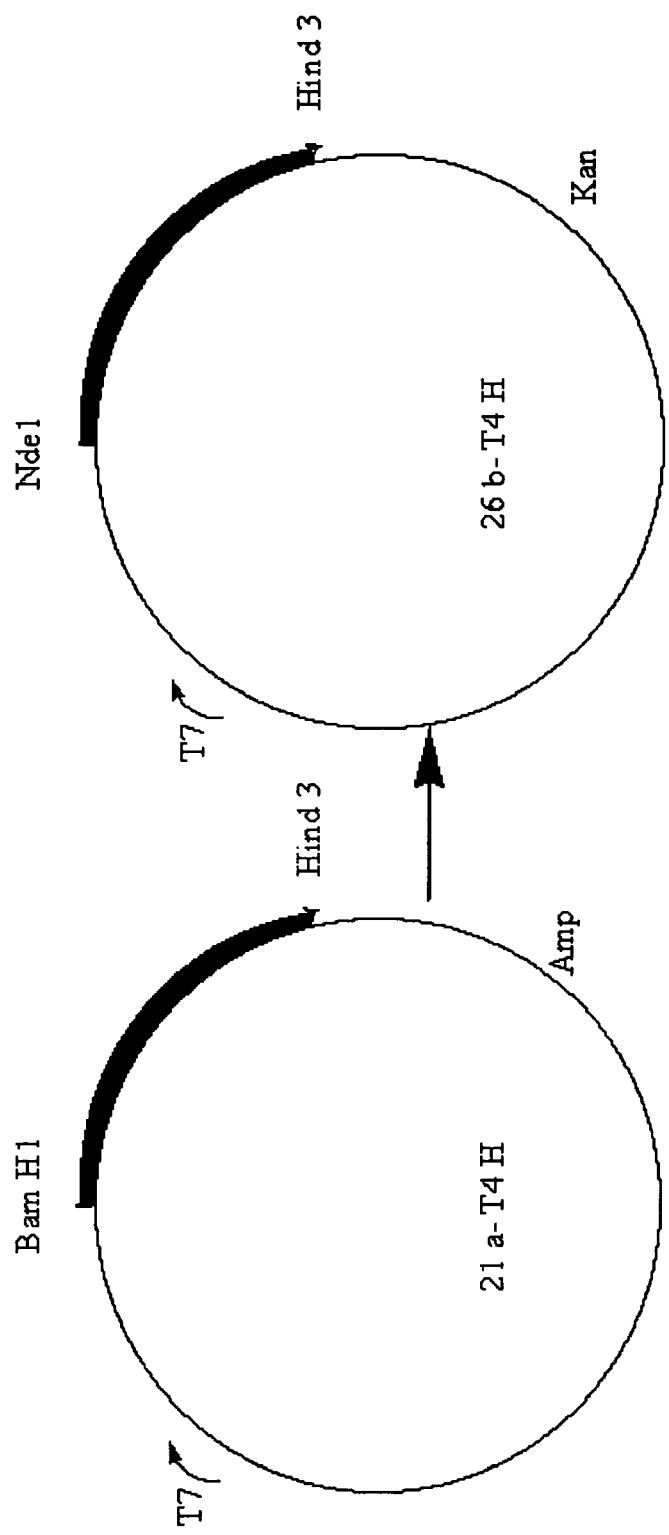
Fig. 4 Cloning and expression of T4 holin gene in bacterial system

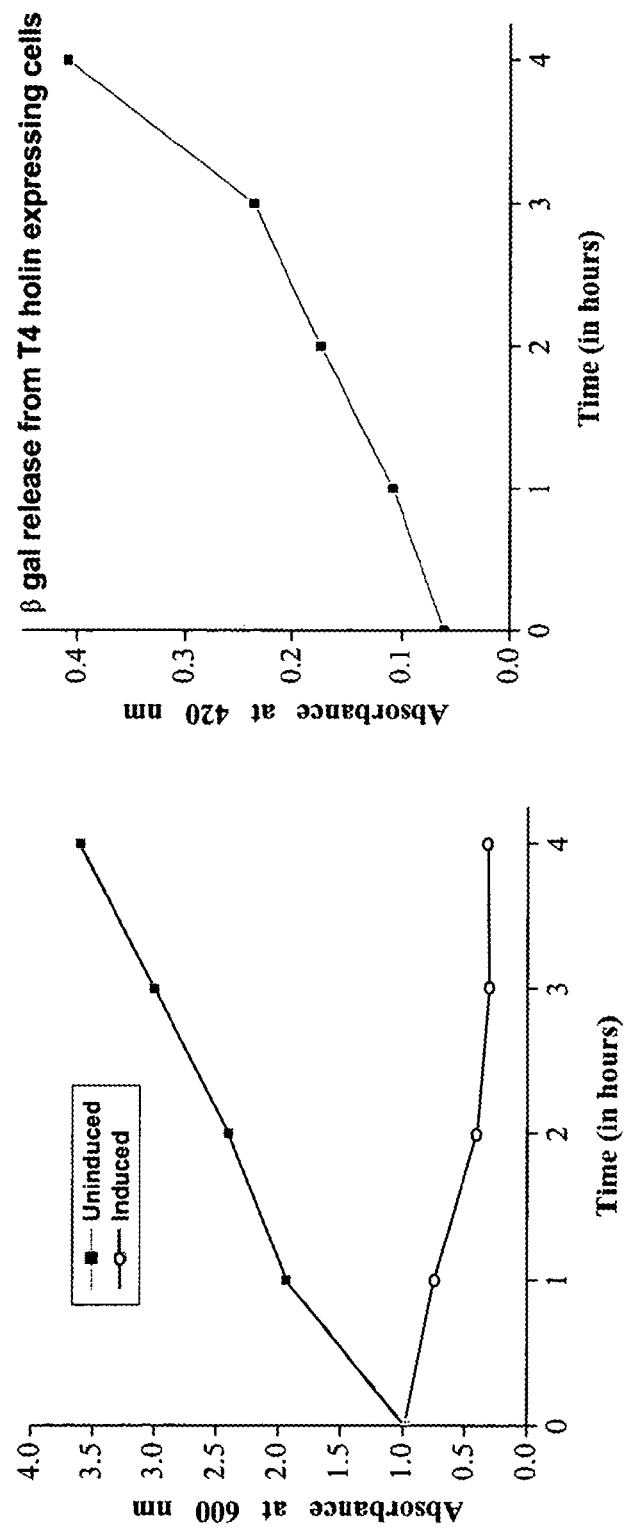
Fig. 5 Expression of T4 holin in BL21 (DE3) cells

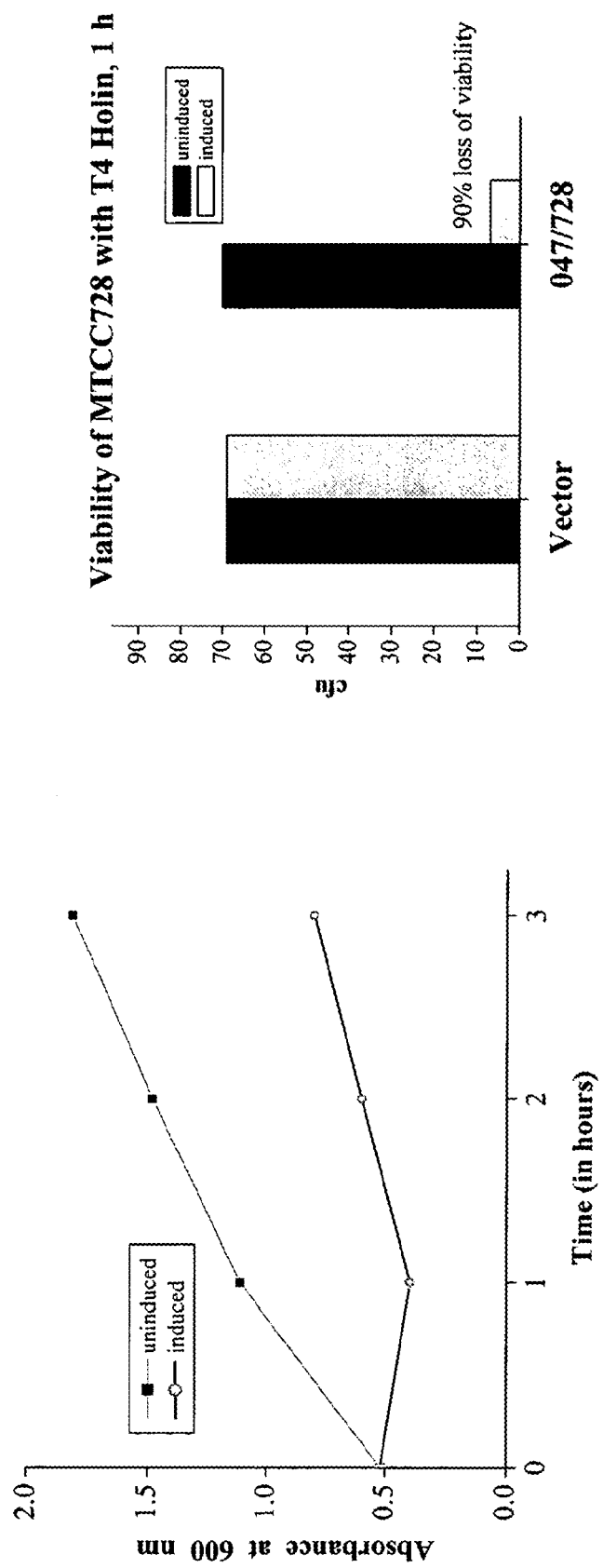
Fig. 6 Expression of T4 holin in MTCC 728 cells

Fig. 7 Expression of T4 holin in MTCC 443 cells
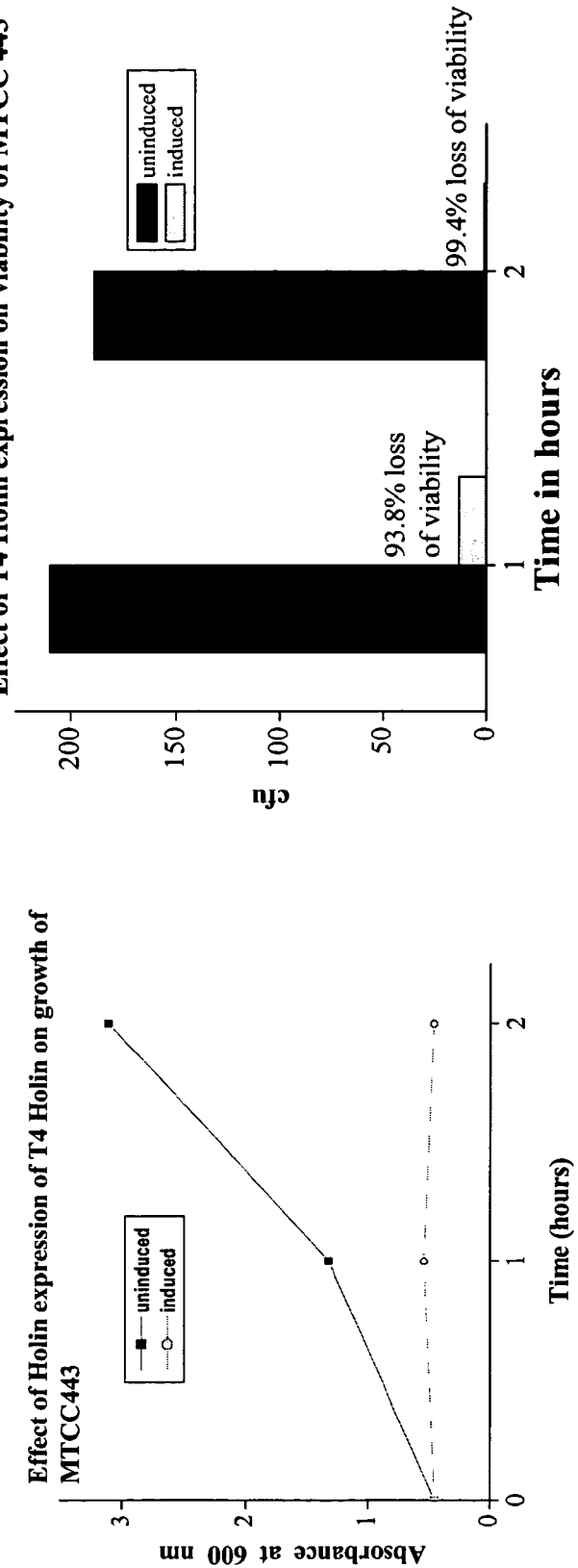

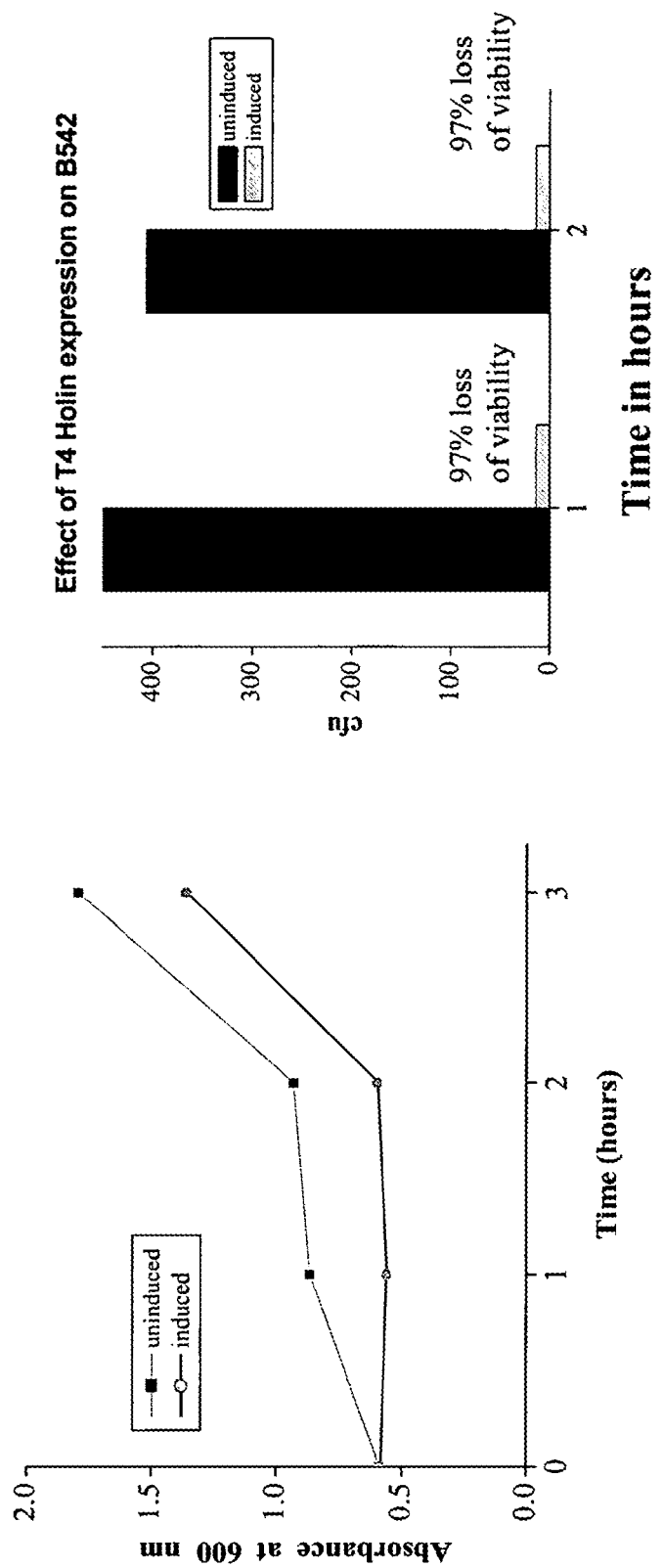
Fig. 8 Expression of T4 holin in B542 cells

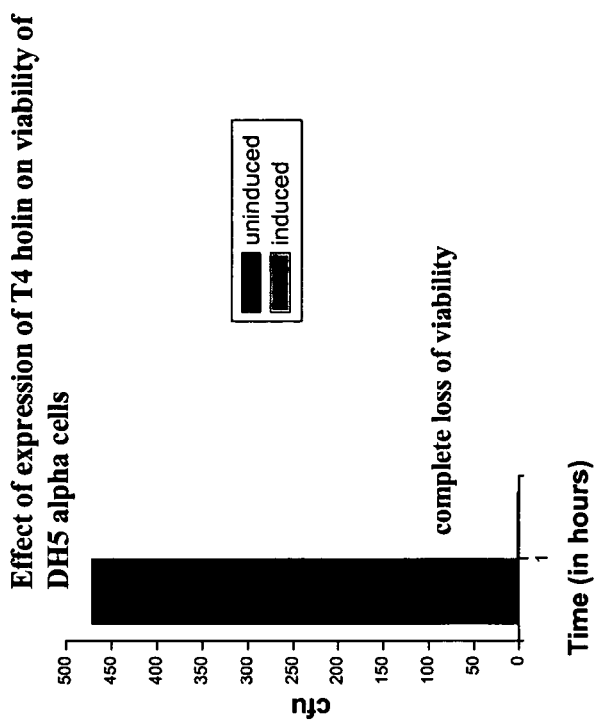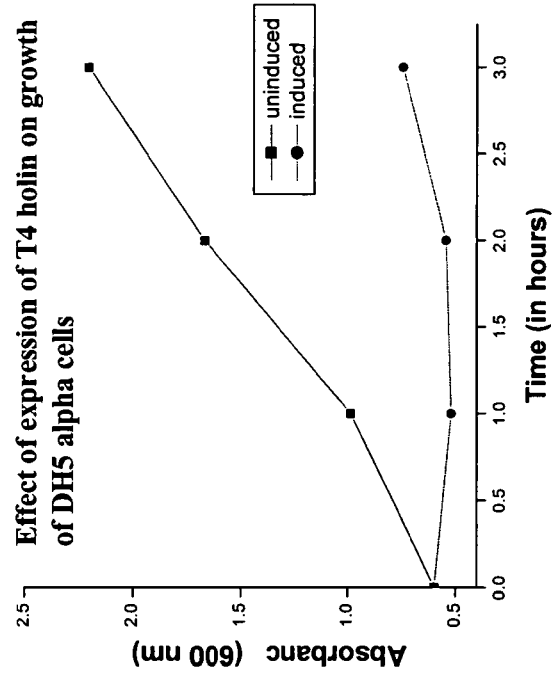
Fig. 9 Effect of expression of T4 holin on growth and viability of DH5α cells

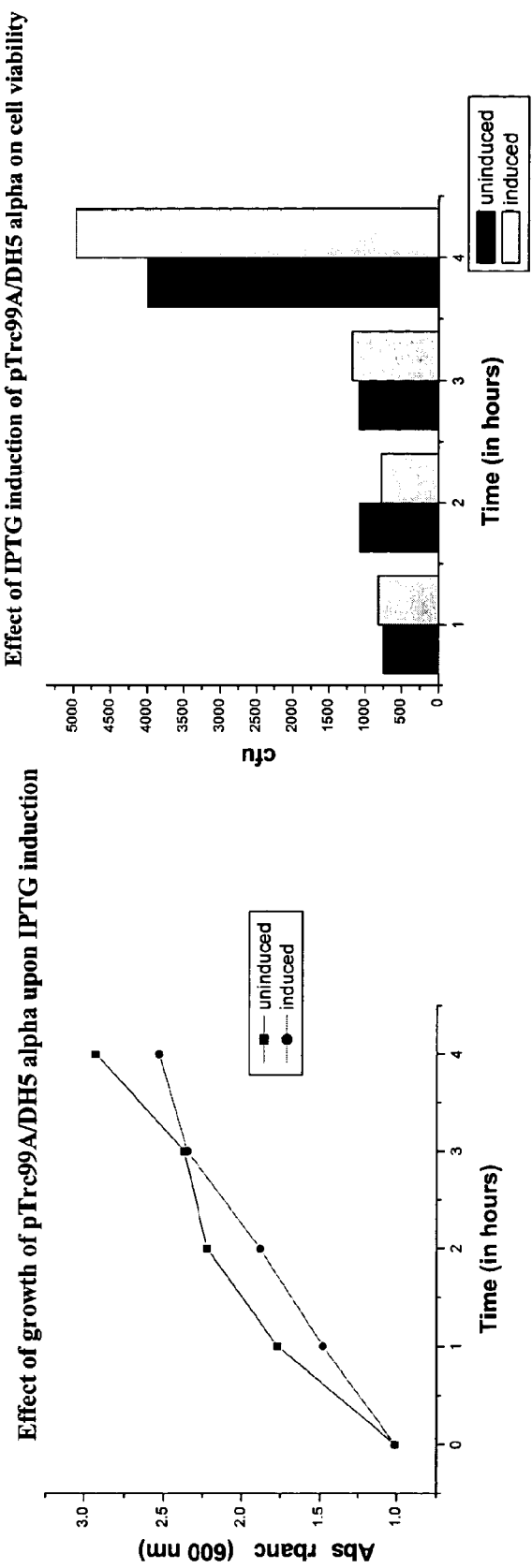
Fig. 10 Effect of IPTG induction of pTrc99A on growth and viability of DH5α cells

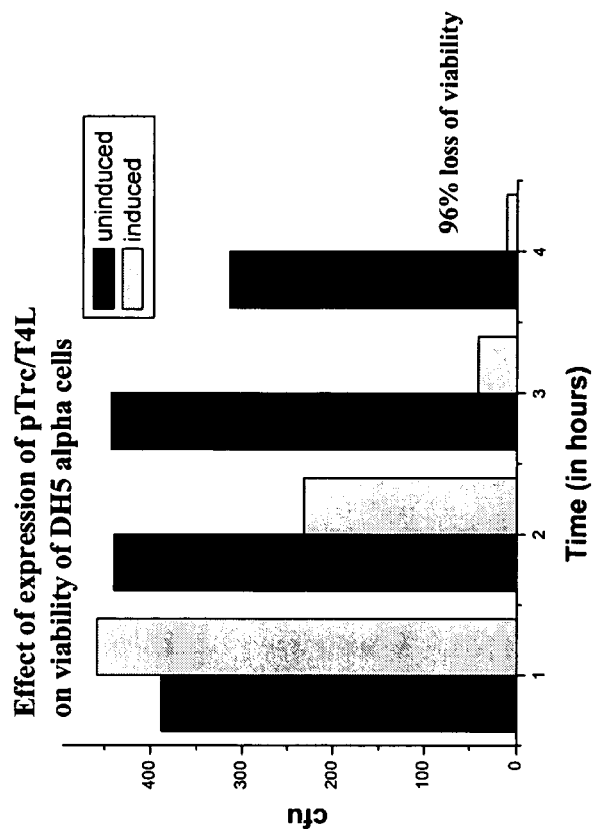
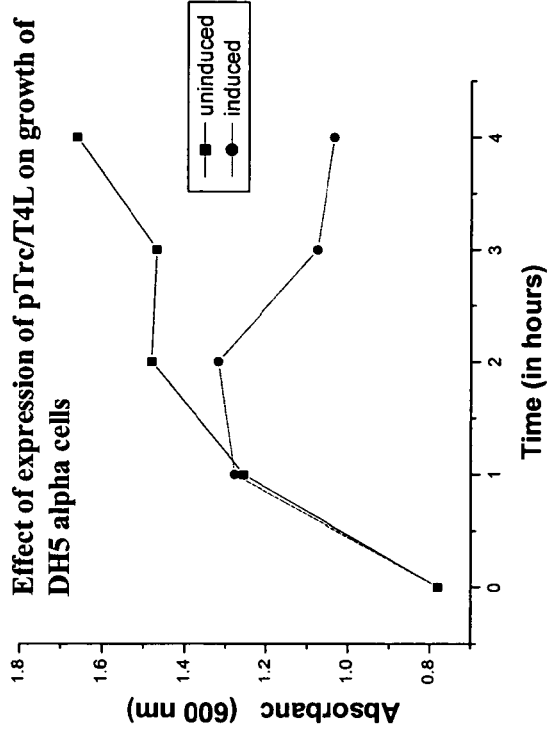
Fig. 11 Effect of expression of pTrc/T4L on growth and viability of DH5α cells

INCAPACITATED WHOLE-CELL IMMUNOGENIC BACTERIAL COMPOSITIONS PRODUCED BY RECOMBINANT EXPRESSION

CROSS-REFERENCE TO RELATED APPLICATIONS

This application is a continuation of U.S. application Ser. No. 10/715,348, filed Nov. 14, 2003, now abandoned, which claims the benefit of U.S. provisional application Ser. No. 60/426,670, filed Nov. 14, 2002, both of which are incorporated herein by reference in their entireties.

FIELD OF THE INVENTION

The invention relates to methods and compositions for production of whole-cell, inactivated immunogenic bacterial compositions that are similar to the live infectious pathogen with respect to immunogenicity, but which are not infectious.

BACKGROUND OF THE INVENTION

The alarming increase in bacterial resistance to available antibiotics, international travel and newly identified infectious diseases have highlighted the need for new effective vaccines. Inactivated whole-cell vaccines are an important component of the approaches emerging to meet these public health needs. The administration of whole-cell vaccines is one of the most well-studied methods of vaccination against bacteria infection. The particular advantages of whole-cell vaccines include the presentation of many antigens (including protective, but yet undefined antigens), minimal chances of side effects when given non-parenterally, zero virulence potential, and adjuvant-like character. Studies in animal models and humans have shown immunogenicity when whole-cell vaccines were administered orally or parenterally. Effective protection against respiratory, enteric and systemic bacterial infections has also been shown. Although only inactivated whole-cell pertussis vaccine has been used to immunize the general public, other whole-cell vaccines have the potential for global use.

There are only two basic types of vaccines: live attenuated and inactivated. The characteristics of live and inactivated vaccines are different, and these characteristics determine how the vaccine is used.

Live Attenuated Vaccines

Live attenuated vaccines are produced by modifying a disease-producing ("wild type") bacteria in the laboratory. Live attenuated vaccines available in the U.S. include live viruses and live bacteria. These wild type viruses or bacteria are attenuated, or weakened, in the laboratory, usually by repeated culturing. In order to produce an immune response, live attenuated vaccines must replicate (grow) in the vaccinated person. A relatively small dose of virus or bacteria is given, which replicates in the body and increases to a volume large enough to stimulate an immune response. Anything that either damages the live organism in the vial (e.g., heat, light), or interferes with replication of the organism in the body (circulating antibody) can cause the vaccine to be ineffective. Although live attenuated vaccines replicate, they usually do not cause disease, such as may occur with the natural (wild) organism. When a live attenuated vaccine does cause "disease," it is usually much milder than the natural disease, and is referred to an adverse reaction. The immune response to a live attenuated vaccine is virtually identical to that produced by a natural infection. The immune system does not differentiate between an infection with a weakened vaccine bacterium and an infection with a wild type bacterium. Live attenuated vaccines are generally effective with one dose, except those administered orally.

However, live attenuated vaccines meet with several limitations, First, live attenuated vaccines may cause severe or fatal reactions as a result of uncontrolled replication (growth) of the vaccine virus. This only occurs in persons with immunodeficiency (e.g., from leukemia, treatment with certain drugs, or HIV infection). In addition depending upon how the vaccine strain was generated, a live attenuated vaccine can sometimes revert back to its original pathogenic (disease-causing) form. To date, this has only been known to occur with live polio vaccine. Active immunity from a live attenuated vaccine may not develop due to interference from circulating antibody to the vaccine virus. Antibody from any source (e.g., transplacental, transfusion) can interfere with grown of the vaccine organism and lead to nonresponse to the vaccine (also known as vaccine failure). Measles vaccine virus seems to be most sensitive to circulating antibody. Polio and rotavirus vaccine viruses are least affected. Live attenuated vaccines are labile and can be damaged or destroyed by heat and light. They must be handled and stored carefully. Currently available live attenuated vaccines include live viruses (measles, mumps, rubella, polio, yellow fever, vaccinia and varicella), and two live bacterial vaccines (BCG and oral typhoid).

Inactivated Vaccines

Inactivated vaccines can be composed of either whole viruses or bacteria, or fractions of either. Fractional vaccines are either protein-based or polysaccharide-based. Protein based vaccines include toxoids (inactivated bacterial toxin), and subunit products. Most polysaccharide-based vaccines are composed of pure cell-wall polysaccharide from bacteria. Conjugate polysaccharide vaccines are those in which the polysaccharide is chemically linked to a protein. This linkage makes the polysaccharide a more potent vaccine. These vaccines are produced by growing the bacteria in culture media, then inactivating it with heat and/or chemicals (usually formalin). In the case of fractional vaccines, the organism is further treated to purify only those components to be included in the vaccine (e.g., the polysaccharide capsule of pneumococcus).

Inactivated vaccines are not alive and cannot replicate. The entire dose of antigen is administered in the injection (as compared to live attenuated vaccines, which provide further "doses" upon replication in the host). Inactivated vaccines cannot cause disease from infection, even in an immunodeficient person. Unlike live antigens, inactivated antigens are usually not affected by circulating antibody. Inactivated vaccines may be given when antibody is present in the blood (e.g., in infancy, or following receipt of antibody-containing blood products). Inactivated vaccines typically require multiple doses. In general, the first dose does not produce protective immunity, but only "primes" the immune system. A protective immune response develops after the second or third dose.

In contrast to live vaccines, in which the immune response closely resembles natural infection, the immune response to an inactivated vaccine is mostly humoral. Little or no cellular immunity results. Antibody titers against inactivated antigens fall over time. As a result, some inactivated vaccines may require periodic supplemental doses to increase or "boost," antibody titers. In some cases, the antigen critical to protection against the disease may not be defined, thus requiring the use of "whole cell" vaccines.

Currently available inactivated vaccines include inactivated whole viruses (influenza, polio, rabies, hepatitis A) and inactivated whole bacteria (pertussis, typhoid, cholera, plague). "Fractional" vaccines include subunits (hepatitis B, influenza, acellular pertussis, typhoid Vi, Lyme disease), toxoids (diphtheria, tetanus, botulinum), pure polysaccharides (pneumococcal, meningococcal, *Haemophilus influenzae* type b) and polysaccharide conjugates (*Haemophilus influenzae* type b and pneumococcal).

In summary, it is recognized that the more similar a vaccine is to the natural disease, the better the immune response to the vaccine. While attenuated vaccines are most promising in this regard, they pose risks of disease in immuno-compromised hosts and reversion to wild-type, pathogenic organisms. Inactivated vaccines avoid these problems, yet can be less desirable in that these vaccines do not mimic natural infection and so may not elicit the relevant immune response or elicit as robust, protective an immune response as might be desired.

One challenge with whole cell vaccines is that, when derived from gram negative bacteria, the composition may contain considerable amounts of endotoxin. Endotoxins are lipopolysaccharides (LPS) (Hitchcock et al, 1986), which are constituents of the bacterial cell wall. Means of inactivation of cells commonly used, such as heating or chemicals (such as formaldehyde), do reduce the levels of endotoxin, but at the same time reduce the antigenic potency of the vaccine itself by the treatment. Systemic exposure to high levels of endotoxins in humans or other mammals results in numerous adverse reactions (Cort & Kindahl, 1980; Culbertson & Osburn, 1980). Clinical signs such as fever, tachypnoea, vomiting as well as changes in the haemodynamics are seen after injection of vaccines containing elevated amount of LPS (Hussain & Ready, 1981).

Vaccines rank among the most effective public health tools for lowering the incidence of the infectious diseases. There is thus a need in the field for safe bacterial vaccines that resemble the infectious organism more closely than the inactivated vaccines, but which have reduced or no significant risk of causing disease in the vaccinated subject. An ideal vaccine would be one that involves use of a whole bacterial cell, but with the toxic effects of the LPS neutralized while retaining the cell intact and resembling the live organism in all other respects. The present invention addresses this need.

REFERENCES

Amann et al. (1983) *Gene* 25: 167-1782; Amann et al. (1988) *Gene*, 69, 301-315; Bloemberg et al. (1997), *Appl. Environ. Microbiol.*, 4443-45514; Chamberlin M. et al., (1970) *Nature (London)*, 228, 227; Chamberlin et al. (1973) *J. Biol. Chem.*, 248, 2235; Cort et al. (1980) *Acta Veterinaria Scandinavia*, 31, 347-358; Culbertson et al. (1980) *Vetenary Scientific Communications*, 4, 3-14; Davanloo et al. (1984) *Proc. Natl. Acad. Sci*, 81, 2035-2039; Dunn et al. (1983) *J. Mol. Biol.*, 166, 477; Golomb et al. (1974) *J. Biol. Chem.*, 249, 2858; Guzman et al. (1992) *J. Bacteriol.*, 177, 4121-4130; Haldimann et al. (1998) *J. Bacteriol.* 180, 1277-1286; Han et al. (1994) *J. Biol. Chem.*, 269(11), 8172-8175; Hitchcock et al. (1986) *J. Bacteriol.*, 166, 699-705; Hussaini et al. (1981) *Vet. Res. Comm.*, 5, 171-175; Ing-Nang Wang et al. (2000) *Annu. Rev. Microbiol.*, 54, 799-825; Luria et al. (1950) *J. Bacteriol.*, 59, 551-560; Martin et al. (1998) *J. Bacteriol.*, 180, 210-217; Murray et al. (1950) *J. Bacteriol.*, 59, 603-615; Schumann et al. (1990) *Science*, 249, 1429; Sherry et al. (1988) *J. Cell Biol.*, 107, 1269; Studier et al. (1986) *J. Mol. Biol.*, 189, 113-130; Studier et al. (1990) *Methods in Enzymology*, 185, 60-63; Wright et al. (1990) *Science*, 249, 1431; Young et al. (1992) *Microbiol. Rev.*, 56, 430-481; Young et al. (1995) *FEMS Micobiol. Rev.*, 17, 191-205; Young et al. (2000) *Trends Microbiol.*, 8, 120-128

SUMMARY OF THE INVENTION

The present invention features incapacitated whole-cell bacterial immunogenic compositions and methods of their production, which compositions are useful to deliver antigens in a manner resembling the live infectious organism in terms of elicitation of a robust immune response, but with reduced risk or no risk of disease. The compositions of the invention are produced by rendering a bacterium bacteriostatic through expression of a recombinant promoter in the bacterial cell, which promoter can be operably linked to a polynucleotide encoding a recombinant gene product. In one embodiment, where the bacterium is a gram negative host, the recombinant gene product provides for reduced toxicity of LPS. In one embodiment, the gene product is a bacteriophage protein, such as endolysin, holin, or ndd.

In one aspect the invention features a method of eliciting an immune response to a bacterial pathogen, the method comprising administering an incapacitated whole cell immunogenic bacterial composition to a subject susceptible to infection by or a disease caused by a pathogenic bacterium. The incapacitated bacterium is produced as a result of expression of a recombinant promoter, which is optionally operably linked to a coding sequence for a recombinant gene product. The immunogenic composition is administered in an amount effective to elicit an immune response to the pathogenic bacterium in the host.

In another aspect the invention features a method of vaccinating a subject against disease caused by a bacterial pathogen, the method comprising administering to a subject susceptible to disease caused by a pathogenic bacterium an incapacitated whole cell bacterial vaccine, the vaccine comprising the pathogenic bacterium incapacitated by expression from a recombinant promoter, which is optionally operably linked to a sequence encoding a recombinant protein. The vaccine is administered in an amount effective to elicit an immune response to the pathogenic bacterium in the subject.

In another aspect, the invention features a method for eliciting an immune response to an antigen, the method comprising administering to a subject an incapacitated whole cell bacterial composition, wherein the composition comprises a bacterium incapacitated by expression from a recombinant promoter, which is optionally operably linked to a sequence encoding a recombinant protein. The composition is administered to the subject in an amount effective to elicit an immune response in the subject to an antigen present in or on the bacterium. In specific embodiments, the recombinant protein is the antigen. The antigen can be endogenous bacterial antigen.

In embodiments of the various aspects above, where the recombinant promoter is operably linked to a recombinant polynucleotide encoding a recombinant protein, the recombinant protein is a protein that binds lipopolysaccharide. In specific embodiments, the recombinant protein comprises a lipopolysaccharide-binding protein (LBP) or an LPS-binding domain thereof. In further specific embodiments, the recombinant protein is not a viral protein of a virus that infects a mammalian cell, e.g., HIV-1 Vpr. Other embodiments include those where the protein or an antibacterial peptide is toxic to the host organism to ensure the cells are inactivated, or where the protein is an immune stimulant or vaccine adjuvant. Further embodiments include those where proteins that negate the effects of host bacterial components on the subject to be immunized (e.g., LPS-binding polypeptides, and the like).

In further embodiments of the aspects above, the recombinant promoter is a strong bacteriophage promoter. In specific embodiments, the bacterium is further modified to express a bacteriophage RNA polymerase for transcription from the bacteriophage promoter. In further related embodiments, the bacteriophage RNA polymerase is operably linked to an inducible promoter. In one specific embodiment, bacteriophage promoter is a T7 promoter and the bacteriophage RNA polymerase is a T7 RNA polymerase.

In further embodiments, the bacterium used to generate the incapacitated bacterium is of a genus selected from the group consisting of Mycobacteria, Staphylococci, *Vibrio, Enterobacter, Enterococcus, Escherichia, Haemophilus, Neisseria, Pseudomonas, Shigella, Serratia, Salmonella, Streptococcus, Klebsiella* and *Yersinia*.

A feature of the invention is that it provides methods for producing an immunogenic bacterial whole cell composition which is incapacitated in a manner that maintains the immunogenicity or antigenicity of the bacterium, but does not allow for recovery of the bacterium and replication and infection in the host.

Another feature of the invention is to provide for methods and compositions to effect a protective immune response against bacterial infections, particularly infections by pathogenic bacteria.

One advantage of the invention is that the incapacitated bacterial vaccines are associated with a substantially reduced risk of causing disease in a vaccinated host compared to live attenuated vaccines, as the incapacitated bacteria do not recover, or only recover at very low rates, from incapacitation according to the invention.

Another advantage of the invention is that antigen against which an immune response is desired when produced in an incapacitated bacterium of the invention is not significantly modified in terms of the antigens presented on the bacterial cell surface or in terms of antigens that are provided as inclusion or aggregate bodies inside bacteria which are processed by the immune system, e.g., following phagocytosis of the bacterium by a macrophage. In contrast, chemically-induced bacterial inactivation can result in cross-linking of surface proteins and irreversible chemical modification of the antigen.

These and other advantages and features of the invention will become apparent to those persons skilled in the art upon reading the details of the animal model and methods of its use as more fully described below.

BRIEF DESCRIPTION OF THE DRAWING

FIG. 1 is set of graphs showing the effect of recombinant green fluorescent protein (rGFP) expression on growth and viability of DE3 *E. coli* cells.

FIG. 2 is a set of graphs showing the effect of recombinant NADH dehydrogenase expression on growth and viability of DE3 *E. coli* cells.

FIG. 3 is a set of graphs showing the effect IPTG induction of expression of the promoter on the pRSET vector on growth and viability of DE3 *E. coli* cells.

FIG. 4 is a schematic illustrating the cloning and expression of the T4 holin gene in a bacterial host.

FIG. 5 is a set of graphs showing the effect of T4 holin upon growth and release of β-galactosidase when expressed in BL21(DE3) *E. coli* cells.

FIG. 6 is a set of graphs showing the effect of T4 holin upon growth and viability when expressed in MTCC 728 *E. coli* cells.

FIG. 7 is a set of graphs showing the effect of T4 holin upon growth and viability when expressed in MTCC 443 *E. coli* cells.

FIG. 8 is a set of graphs showing the effect of T4 holin upon growth and viability when expressed in B542 *E. coli* cells.

FIG. 9 is a set of graphs showing the effect of T4 holin upon growth and viability when expressed in MTCC 728 *E. coli* cells.

FIG. 10 is a set of graphs showing the effect of IPTG induction of pTrc99A on growth and viability of DH5α *E. coli* cells.

FIG. 11 is a set of graphs showing the effect of pTrc/T4L on growth and viability when expressed in DH5α *E. coli* cells.

Before the present invention is described, it is to be understood that this invention is not limited to particular methodology, protocols, bacteria, animal species or genera, constructs, and reagents described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a promoter" includes a plurality of such promoters and reference to "the host cell" includes reference to one or more host cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods and compositions relating to production of incapacitated whole cell bacteria, which bacteria are generated by expression of a recombinant promoter, which is optionally operably linked to a recombinant polynucleotide encoding a gene product. Expression from the promoter is at a level sufficient to render the host bacterium bacteriostatic. In one embodiment of particular interest, where the bacterium is a gram negative host, the recombinant gene product provides for reduced toxicity of LPS, e.g., through expression of a protein such a lipopolysaccharide-binding protein (LBP). In other embodiments, the recombinant gene product is toxic to the host cell, or induces a more robust immune response, e.g., by attracting immune cells or increasing an active immune response.

Specific aspects of the invention will now be described in more detail. The incapacitated whole cell bacteria will be useful as vaccine immunogens. See, e.g., Levine, et al. (eds. 1997) New Generation Vaccines Dekker ISBN 0824700619; Schulz and Dodds (eds. 1999) Veterinary Vaccines and Diagnostics Academic Press ISBN 0120392429; and Kirkpatrick and Alston (2003) Curr. Op. Infect. Dis. 16:369-74.

Definitions

By "incapacitated" in the context of an incapacitated bacterial cell produced according to the invention, is meant that the bacterial cell is in a state of irreversible bacteriostasis. While the bacterium retains its structure—and thus retains the immunogenicity, antigenicity, and receptor-ligand interactions associated with a wild-type bacterium—it is not capable of replicating due to the depletion of host factors due to the expression from a recombinant promoter.

By "isolated" is meant that the material is at least 60%, by weight, free from the proteins and naturally-occurring organic molecules with which it is naturally associated. Preferably, the material is at least 75%, more preferably at least 90%, and most preferably at least 99%, by weight, the material of interest. "Isolated" thus encompasses preparations that are enriched for the desired material.

The terms "polynucleotide" and "nucleic acid", used interchangeably herein, refer to a polymeric forms of nucleotides, including ribonucleotides, deoxynucleotides, or mixed forms. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide" and "protein", used interchangeably herein, refer to a polymeric form of amino acids of any length, which can include coded and non-coded amino acids, chemically or biochemically modified (e.g., post-translational modification such as glycosylation) or derivatized amino acids, polymeric polypeptides, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

"Recombinant host cells", "host cells", "cells", "cell lines", "cell cultures", and other such terms denoting microorganisms or higher eukaryotic cells cultured as unicellular entities refer to cells which have been used as recipients for recombinant vector or other transfer DNA, and include the progeny of the original cell which has been transfected. Recombinant bacterial host cells are of particular interest in the present invention. It is understood that the progeny of a single parental cell may not necessarily be completely identical in morphology or in genomic or total DNA complement as the original parent, due to natural, accidental, or deliberate mutation.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and can be translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Heterologous" means that the materials are derived from different sources (e.g., from different genes, different species, etc.).

"Transformation", as used herein, refers to the insertion of an exogenous polynucleotide into a host cell, irrespective of the method used for the insertion, for example, direct uptake, transduction, F-mating or electroporation. The exogenous polynucleotide may be maintained as a non-integrated vector, for example, a plasmid, or alternatively, may be integrated into the host genome.

The terms "individual," "subject," "host," and "patient," are used interchangeably herein and refer to any subject having a bacterial infection amenable to treatment using the immunogenic compositions of the invention, and for whom treatment or therapy is desired. Mammalian subjects and patients, particularly primate subjects or patients are of particular interest. Other subjects may include livestock or companion animals, e.g., cattle, dogs, cats, guinea pigs, rabbits, rats, mice, horses, and so on.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, i.e., arresting its development; or relieving the disease symptom, i.e., causing regression of the disease or symptom.

By "infecting bacterium" is meant a bacterium that has established infection in the host, and which may be associated with a disease or undesirable symptom as a result. Generally, infecting bacteria of interest are pathogenic bacteria, and may include a culture of multiple bacteria which together act to cause the pathology. Treatment may require elimination of a single, or multiple types of bacteria.

By "drug-resistant bacteria" or "antibiotic-resistant bacteria" is meant a bacterial strain that is resistant to growth inhibition or killing by an antibiotic. Multi-drug resistant bacteria are resistant to two or more antibiotics. Drug resistance can encompass, for example, ineffective killing of the infecting bacteria such that at least an infectious dose remains in the subject and the infection continues, resulting in continued symptoms of the associated infectious disease or later evidence of such symptoms. Drug resistance can also encompass inhibiting growth of the drug-resistant bacteria until such time therapy is discontinued, after which the bacteria begin to replicate and further the infectious disease.

By "inhibition of bacterial growth" in the context of infection of an incapacitated bacterial cell according to the invention is meant that, following infection of the bacteria, the bacterial host cell's normal transcriptional and/or translational mechanisms are compromised such that the infected bacteria does not undergo substantial cell division (replication) and is caused to enter a state of bacteriostasis. The stasis causes pathogenic effects to also regress.

The term "protective immunity" means that a vaccine, immunogenic composition or immunization schedule that is administered to a mammal induces an immune response that prevents, retards the development of, or reduces the severity of a disease that is caused by a pathogenic bacterium or diminishes or altogether eliminates the symptoms of the disease.

The phrase "in a sufficient amount to elicit an immune response to epitopes present in said preparation" means that there is a detectable difference between an immune response indicator measured before and after administration of a particular immunogenic composition (e.g., vaccine preparation). Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion; binding detection assays of, for example, spot, Western blot or antigen arrays; cytotoxicity assays, etc.

The terms "immunogenic bacterial composition" and "immunogenic composition" are used interchangeably herein to mean a preparation capable of eliciting a cellular and/or humoral immune response in a subject when administered in a sufficient amount to elicit an immune response to epitopes present in said preparation. Such immunogenic compositions can find use as a vaccine.

A "surface antigen" is an antigen that is present in a surface structure of a bacterial cell (e.g. the outer membrane, inner membrane, periplasmic space, capsule, pili, etc.).

The term "immunologically naïve" with respect to a particular bacterial pathogen denotes an individual (e.g., a mammal such as a primate patient) that has never been exposed (through infection or administration) to the specific bacterial pathogen or to an antigen composition derived from such bacteria in sufficient amounts to elicit protective immunity, or if exposed, failed to mount a protective immune response.

As used herein, the term "antibody" refers to a polypeptide or group of polypeptides which are comprised of at least one antibody combining site. An "antibody combining site" or "binding domain" is formed from the folding of variable domains of an antibody molecule(s) to form three-dimensional binding spaces with an internal surface shape and charge distribution complementary to the features of an epitope of an antigen, which allows an immunological reaction with the antigen. An antibody combining site may be formed from a heavy and/or a light chain domain ($V_H$ and $V_L$, respectively), which form hypervariable loops which contribute to antigen binding. The term "antibody" includes, for example, vertebrate antibodies, hybrid antibodies, chimeric antibodies, altered antibodies, univalent antibodies, the Fab proteins, and single domain antibodies. An "anti-idiotype" antibody refers to a type of antibody which mimics the structure of an antigen to which another antibody is specific.

Production of Incapacitated Bacteria

In general, incapacitated bacteria of the invention are produced by expression, particularly hyper-expression, from a recombinant promoter. Expression from the recombinant promoter is at a level sufficient to render the bacterial host bacteriostatic. The following provides description of specific embodiments of the invention.

Expression from a Heterologous Promoter, Optionally Operably Linked to a Recombinant Protein-Encoding Sequence, in a Bacterial System:

In general, the invention provides for production of incapacitated bacteria (e.g., the bacterial host is rendered bacteriostatic) by expression of a heterologous promoter at a level for production sufficient to render the bacteria bacteriostatic.

In one embodiment, the promoter is a strong bacteriophage promoter, such as a T7 promoter and the bacteria is modified to express a recombinant compatible bacteriophage polymerase, such as T7 RNA polymerase. The RNA polymerase of bacteriophage T7 is very selective for specific promoters that are rarely encountered in DNA unrelated to T7 DNA (M. Chemberlin et al., Nature (London), 228, 227, 1970; J. J. Dunn and F. W. Studier, J. Mol. Biol., 166, 477, 1983). Efficient termination signals are also rare, so that T7 RNA polymerase makes complete transcripts of any DNA that is placed under the control of a T7 promoter. T7 RNA polymerase is a very active enzyme and elongates chains five times faster than does E. coli RNA polymerase (M. Chamberlin and J. Ring, J. Biol. Chem., 248, 2235 (1973); M. Golomb and M. Chemberlin, J. Biol Chem., 249, 2858 (1974).

T7 RNA polymerase transcribes actively and selectively under the control of the T7 promoter. Transcription by T7 RNA polymerase is so active that transcription by the host RNA polymerase cannot compete and almost all the transcription in the cell rapidly becomes due to T7 RNA polymerase.

A single molecule of active T7 RNA polymerase is sufficient to trigger a response of autocatalytic increase in both the level of T7 RNA polymerase and in the rate of transcription of a plasmid wherein the gene is cloned along with its promoter (Davanloo et al 1984). Therefore, incapacitation may be achieved even by simply expressing T7 RNA polymerase alone.

In one embodiment, the promoter is operably linked to a nucleic acid encoding a recombinant heterologous protein. In such applications the most important parameter is the fractional abundance of the recombinant heterologous protein at the time the culture is harvested. Different fermentation schemes can achieve identical fractional abundances. The expression module may be so arranged as to yield a reasonable fractional synthetic rate throughout the growth period and harvest the culture at the highest possible cell concentration. Conversely, the heterologous gene may be induced fully at a stage late in fermentation to obtain and harvest at maximal abundance of the protein of interest. The focus in such procedures is on the heterologous protein being synthesized, such that the bacterial host is rendered incapable of expression of endogenous genes at a level sufficient to maintain bacterial cell viability. Thus, the gene may be optimized by codon usage to produce maximum efficiency in translation by the host.

In a related embodiment, the strong promoter is operably linked to a nucleic acid encoding a recombinant, e.g., heterologous, protein. The data described in the Examples below indicates that "hyper expression" of any recombinant protein in a bacterial system under T7 promoter system, leads to total loss of bacterial viability. Examples of such proteins include green fluorescent protein (GFP) and NADH dehydrogenase. Thus, the present inventors have found that the protein need not be one that has activity itself in inactivating the bacterial host cell transcription or translation machinery, or otherwise itself has activity in inhibiting bacterial growth. In particular embodiments, the recombinant protein is other than a eukaryotic viral protein, such as HIV-1 Vpr. In other embodiments, the protein is toxic to the producing cell, ensuring that the cell is inactivated. In yet other embodiments, the protein is a cytokine or other immunoregulatory protein which induces the immune system to mount a more robust immune response to the immunogen. Generally, the proteins themselves will be minimally immunogenic, e.g., may be of subject origin.

In another embodiment, the recombinant promoter is an inducible strong promoter. In still another embodiment, the bacteria is modified to contain two recombinant promoters: 1) a first recombinant strong promoter, which is optionally operably linked to a polynucleotide encoding a gene product; and 2) a second recombinant inducible promoter, which promoter is operably linked to a polynucleotide encoding an RNA polymerase that acts upon the first strong promoter. For example, the first promoter can be a strong bacteriophage promoter, such as a T7 promoter, and the second inducible promoter is operably linked to a polynucleotide encoding a bacteriophage RNA polymerase specific for the first promoter, such as T7 RNA polymerase.

The inducible promoter can be any suitable inducible promoter, e.g., lac promoter or derivative thereof; trp promoter or derivative thereof; arabinose promoter or derivative thereof; tetracycline inducible promoter; and the like. In the Examples below, the inventors have demonstrated that induction of synthesis with IPTG of T7 RNA polymerase present on the chromosome (DE3 lysogen) under lacUV5 promoter in the laboratory strain BL21 DE3 leads to loss of viability of the cells.

In another embodiment, the recombinant, e.g., heterologous, protein is a protein that is selectively and highly toxic to the bacterial host alone. In this embodiment, an expression level required to incapacitate the bacterial host cell is relatively low, i.e., low levels of expression are sufficient to effect incapacitation of the bacterial cell. For example, a protein that is inserted into the inner membrane of the bacterial cell that thereby destroys the membrane potential; or a protein that effects inactivation of bacterial ribosomes. In such cases, induction of the heterologous gene would be followed shortly thereafter by cessation of protein synthesis.

Expression of Heterologous Protein of Biological Use:

In another embodiment, the invention involves expression of a recombinant protein from the recombinant promoter in an amount that provides for a biologically relevant activity. In one embodiment, the biologically relevant activity is reduction of toxicity of endotoxin (LPS), such as an LPS-binding protein (e.g., LPS-binding protein (LBP), bactericidal-permeability increasing protein (BPI), U.S. Pat. Nos. 5,089,274; 5,171,739; 5,198,541); CAP18 (Larrick et al. Biochem Biophys Res Commun. 1991 Aug. 30; 179(1):170-5); and the like. The concept is not limited to the LPS-binding protein alone and may be extended to several other proteins and peptides that would aid in combating bacterial infection directly or indirectly. It also applies to use of such incapacitated cells as vehicles for delivering biologically useful peptides or proteins or other molecules to target tissues or cells of humans and animals.

Other embodiments include cytokines, e.g., IL-4, IL-13, and others, which induce particular immune responses. Other genes may attract dendritic cells, helper T cells, resting macrophages etc., to the site of the innoculation. These may even include prominent cell surface antigens of the target vaccine cells themselves, which would amplify the antigenic signal. Immune adjuvants may be used, preferably derived from the subject, thereby minimizing the likelihood of an immune response to the expressed protein, but assisting the immune system in responding to the vaccine.

Complex mechanisms come into play in both vertebrates and invertebrates in response to infection with gram negative bacteria. The various defense mechanisms are triggered by recognition of the LPS (endotoxin) present on the outer membrane of these bacteria. Leukocytes respond to LPS at very low concentrations and a cascade of events follows involving several effector molecules among which excessive secretion of Tumor Necrosis Factor (TNF) plays a major role in mediating the endotoxic effects (B. Sherry & A. Cerami, 1988). The host response ends in elimination of the pathogen or may lead to severe symptoms of irreversible shock, sepsis, multi-organ failure and finally death.

LPS binding protein (LBP) is an approximately 60 kDa acute phase protein that is produced by hepatocytes. This protein strongly binds to LPS and has been shown to play an important role in the handling of LPS by the host. A number of functions of LBP have been reported. First, LBP transfers LPS to the LPS receptor CD14 on mononuclear phagocytes, leading to an 100-1,000-fold increased sensitivity of the cells to LPS. Furthermore, LBP can enhance the response of CD14 negative cells by acceleration of LPS binding to soluble CD14, a complex that stimulates these cells. Blockade of CD14 with antibodies prevented synthesis of TNFa by whole blood incubated with LPS (S D Wright et al., 1990). Next, LBP transfers LPS into High Density Lipoprotein (HDL) which effectively neutralizes its biological potency. LBP was demonstrated to protect mice from septic shock caused by LPS or gram negative bacteria.

LBP contains two domains, one which binds to LPS and other which binds to CD14. It has been shown (Han J et al, 1994) that LBP, truncated at amino acid residue 197, binds LPS but does not transfer LPS to CD14. Thus, appropriately modified fragments of LBP can be agents to bind LPS discharged by gram-negative bacteria, see, e.g., U.S. Pat. No. 5,731,415 (describing LBP fragments that bind LPS and LPS-binding proteins). See also Schumann et al. "Structure and function of lipopolysaccharide binding protein" Science. 1990 Sep. 21; 249(4975):1429-31.

Thus in one aspect, the invention features cloning and expression of a polypeptide comprising the LPS-binding domain of LBP, e.g., an LBP fragment that does not contain a functional CD14-binding domain. The incapacitated bacterial cells are modified to express the protein at a level sufficient to render the bacterial host incapacitated (e.g., bacteriostatic). Expression of the LPS-binding protein provides for production of a store of this protein in the host cell. When released from the bacterial cell, the LPS-binding protein effectively scavenges the LPS in circulation by competing with native LBP present in the subject. The gene encoding the desired protein can be optimized for codon usage to maximize expression levels.

Expression of Phage Gene Products in Bacteria:

In another embodiment, the bacterial host is incapacitated by expression of one or more bacteriophage proteins, which proteins may be expressed from an inducible promoter, and which proteins are expressed at a level sufficient to incapacitate the bacterial host.

For example, within a few minutes after the T4 phage infects E. coli infection, the structure of the bacterial nucleoid changes dramatically. The bacterial nucleoid, present in the center is dispersed to the periphery, distributed along the inner membrane (Murray et al, 1950; Luria and Human, 1950). This phenomenon is known as nuclear disruption and is brought about by the gene product of T4 ndd gene. Thus T4 ndd is a suitable recombinant protein for expression in this embodiment of the invention. This could also include other bacteriophage, viral, bacterial, or other enzymes that when expressed inactivate the cell by other means such as degradation of the nucleic acids (nucleases) or degradation of proteins (proteases) or via interruption of critical processes in the bacterial cell.

Host lysis by most bacteriophages requires two phage coded proteins—Holin and Endolysin (Wang, I. N—et al., 2000; Young, R. et al., 2000). While endolysins are muralytic enzymes that are involved in cell wall degradation (Young. R, 1993; Young. R & Blasi. U, 1995), it is the holins that determine the specific time of cell lysis. Holins are small membrane proteins that accumulate and oligomerize in the membrane and lead to permeabilization of the membrane by formation of a hole in the membrane that makes the cell wall amenable to the endolysin (Young. R & Blasi. U, 1995; Ing-Nang Wang et al., 2000).

The holin gene of the temperate bacteriophage PhiO1205 which infects Streptococcus thermophilus when cloned on a plasmid and expressed in E. coli expression system has been shown to cause cell death and leakage of intracellular enzymes into the growth medium. The expression of a cloned viral gene (gene e of PhiX174) in gram-negative bacteria has also been shown to result in lysis of these bacteria by formation of a specific transmembrane tunnel structure built through the cell envelope complex. During lysis the cell content is expelled by the osmotic pressure inside the cell resulting in bacterial ghosts. Both holin and endolysin are suitable bacteriophage proteins suitable for expression in this embodiment of the invention for production of an immunogenic, incapacitated bacteria composition.

The different means of generating incapacitated bacterial cells for use as whole cell vaccines described have the following main advantages:
  Retention of the broad array of pathogen specific antigens, particularly epitopes which may be derived from complex surface structures;
  Bacteria are inactivated through a process that preserves much of the bacteria's native structure, which should result in an enhanced protective immune response;
  Dead bacteria are taken up by macrophages and dendritic cells, resulting in the induction of cellular immune responses;
  Suited as vaccines for both mucosal and intramuscular administration; and
  Can be designed to carry an array of antigens from other pathogens.

Bacterial Pathogens for which Incapacitated Whole Cell Vaccines can be Generated According to the Invention Most any suitable bacterial host of interest can be used to produce an incapacitated bacterium according to the invention. Of particular interest is the development of immunogenic, incapacitated bacterial compositions for clinically-important bacterial species and strains. Bacteria that are pathogenic for an animal, particularly a mammal, more particularly a primate (e.g., human), are of particular interest for use in the production of immunogenic incapacitated bacterial compositions of the invention. Specific examples of bacteria suitable for primate use include:

1. Clinically important members of the family Enterobacteriaceae, including, but not limited to:
    a. Clinically important strains of *Escherichia*, with *E. coli* being of particular interest;
    b. Clinically important strains of *Klebsiella*, with *K. pneumoniae* being of particular interest;
    c. Clinically important strains of *Shigella*, with *S. dysenteriae* being of particular interest;
    d. Clinically important strains of *Salmonella*, including *S. abortus-equi*, *S. typhi*, *S. typhimurium*, *S. newport*, *S. paratyphi-A*, *S. paratyphi-B*, *S. potsdam*, and *S. pollurum*;
    e. Clinically important strains of *Serratia*, most notably *S. marcescens*
    f. Clinically important strains of *Yersinia*, most notably *Y. pestis*
    g. Clinically important strains of *Enterobacter*, most notably *E. cloacae*;
2. Clinically important Enterococci, most notably *E. faecalis* and *E. faecium*
3. Clinically important *Haemophilus* strains, most notably *H. influenzae*;
4. Clinically important Mycobacteria, most notably *M. tuberculosis, M. avium-intracellulare, M. bovis*, and *M. leprae*;
5. *Neisseria gonorrhoeae* and *N. meningitidis*;
6. Clinically important *Pseudomonads*, with *P. aeruginosa* being of particular interest;
7. Clinically important Staphylococci, with *S. aureus* and *S. epidermidis* being of particular interest;
8. Clinically important Streptococci, with *S. pneumoniae* being of particular interest; and
9. *Vibrio cholera*

Additional bacterial pathogens, far too numerous to mention here, particularly those in which drug-resistance has developed, can also be used to produce immunogenic, incapacitated bacterial composition according to the invention. Similar lists of clinically important bacteria species and strains can be generated for other animals, e.g., livestock and companion animals. Each target species will have particular bacterial infections of significance to health, and bacteriophage which target such infections.

Recombinant Antigens for Expression in a Bacterial Host Cell and Production of Immunogenic Compositions In one embodiment, the bacterial host cell can be modified to express an antigenic molecule to which an immune response is desired, e.g., for production of antibodies to a particular antigen.

A DNA sequence which encodes an antigenic molecule, or fragment thereof (e.g., epitope), from either a heterologous or endogenous organism, which when expressed in bacteria produces protective immunity against the organism or against a condition or disorder caused by the organism, can be isolated for use in the immunogenic preparations of the present invention. In one embodiment, the antigen is a surface antigen. In another embodiment, the organism is a pathogenic microorganism. In yet another embodiment, the antigenic molecule, or fragment thereof, is characteristic of cancer and provides protective immunity against the cancer or elicits an immune response against the cancer resulting in reduction or elimination of the cancer from a subject.

Antigenic molecules, or fragments thereof, may be found on pathogens, such as bacteria, parasites, viruses or fungi. Bacteria, parasites, viruses and fungi of interest include, but are not limited, to those listed in Table I below.

TABLE 1

| PARASITES: | BACTERIA: |
|---|---|
| *Plasmodium* spp. (e.g., *P. falciparum*, *P. vivax*, *P. ovale*, *P. malariae*) | *Vibrio* spp. (e.g. *V. cholerae*) |
| | *Neisseria* spp. (e.g., *N menigitidis*, *N. gonorrhoeae*) |
| *Eimeria* spp. | *Corynebacteria diphtheriae* |
| *Schistosoma* spp. | *Clostridium tetani* |
| *Trypanosoma* spp. | *Branhamella catarrhalis* |
| *Babesia* spp. | *Bordetella pertussis* |
| *Leishmania* spp. | *Haemophilus* spp. (e.g., *H. influenzae*) |
| *Cryptosporidia* spp. | *Chlamydia* spp. |
| *Toxoplasma* spp. | *Escherichia* spp. (e.g., *E coli*) |
| *Pneumocystis* spp. | *Bacillus anthracis* |
| | *Borrelia burgdorferi* |
| | *Shigella* spp. (e.g., *S. dysenteriae*) |
| | *Pseudomona* spp. (e.g., *P. aeuruginosa*) |
| | *Enterococcus* spp. (e.g, *E. faecalis*, *E. faecium*) |
| | *Streptococcus* spp. (e.g., *S. pneumoniae*) |
| | *Staphylococcus* spp. (e.g., *S. aureus*, *S. epidermidis* |
| | *Salmonella* spp. (e.g., *S. abortus-equi*, *S. typhi*, *S. typhimurium*, *S. newport*, *S. paratyphi-A*, *S. paratyphi-B*, *S. potsdam*, and *S. pollurum*) |
| | *Serratia* spp. (e.g, *S. marcescens*) |
| | *Klebsiella* spp. (e.g., *K. pneumoniae*) |
| | *Yersinia* spp. (e.g., *Y. pestis*) |
| | *Enterobacter* spp. (e.g., *E. cloacae*) |
| | *Serratia* spp. |
| | *Mycobacterium* spp. (e.g., *M. tuberculosis*, *M. avium-intracellulare*, *M. bovis*, *M. leprae*) |
| | *Rickettsia* spp. (e.g., *R. prowazekii*, *R. typhi*, *R. rickettsii*) |
| | *Rochalimaea quintana* |
| | *Coxiella burnetii* |
| FUNGI: | VIRUSES: |
| *Candida* spp. (e.g., *C. albicans*) | Human Immunodeficiency virus, type I |
| *Cryptococcus* spp. (e.g., *C. neoformans*) | Human Immunodeficiency virus, type II |
| *Blastomyces* spp. (e.g., *B. dermatitidis*) | Simian Immunodeficiency virus |
| | Human T lymphocyte virus, type I, II and III |
| *Histoplasma* spp. (e.g., *H. capsulatum*) | Respiratory syncytial virus |
| | Hepatitis A virus |
| *Coccidioides* spp. (e.g., *C immitis*) | Hepatitis B virus |
| | Hepatitis C virus |
| *Paracoccidioides* spp. (e.g., *P. brasiliensis*) | Non-A, Non-B Hepatitis Virus |
| | Herpes simplex virus, type I |
| *Aspergillus* spp. | Herpes simplex virus, type II |
| | Cytomegalovirus |
| | Influenza virus |
| | Parainfluenza virus |
| | Poliovirus |
| | Poxvirus |
| | Rotavirus |
| | Coronavirus |
| | Rubella virus |
| | Measles virus |
| | Mumps virus |
| | Varicella |
| | Epstein Barr virus |
| | Adenovirus |
| | Papilloma virus |
| | Flaviviridae (e.g., yellow fever virus, dengue fever virus, Japanese encaphilitis virus) |

In addition, antigenic molecules of cancer cells can be used. Antigens characteristic of cancer cells and useful in the vaccine preparations of the present invention include, but are not limited to, MAGE, MUC1, HER2/neu, CEA, pS3, Tyrosinase, MART-1/melan A, gp 100, TRP-1, TRP-2, PSA, CDK4-R24C, BCR/ABL, Mutated K-ras, ESO-1, CA15-3, CA125, CA19-9, CA27.29, TPA, TPS, Cytokeratin 18, and Mutated p53.

Where antigens have not yet been characterized, potentially useful antigens for vaccine formulations can be identified by various criteria, such as the antigen's involvement in neutralization of a pathogen's infectivity (Norrby, E., 1985, Summary, in Vaccines 85, Lerner, R. A., R. M. Chanock, and F. Brown (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen.

Immunoreactive molecules can be identified and characterized by methods known in the art. Monoclonal antibodies can be generated to the surface or other molecules of a pathogen to identify those that are capable of being recognized by the antibodies. Alternatively, small synthetic peptides conjugated to carrier molecules can be tested for generation of monoclonal antibodies that bind to the sites corresponding to the peptide on the intact molecule (see, e.g., Wilson, I. A., et al., 1984, Cell 37:767).

Genetically engineered bacteria useful in the invention can be created by employing recombinant DNA technology. A nucleotide sequence which encodes an antigenic molecule of interest is inserted into an expression vector, transformed or transfected into an appropriate bacterial host cell and cultivated under conditions suitable for expression. These procedures are well known in the art and are described generally in Sambrook, et al., Molecular Cloning, A Laboratory Manual, Cold Spring Harbor Press, Cold Spring Harbor, N.Y. (1989).

The nucleotide sequence encoding an antigenic molecule may also be fused to with a nucleic acid, bacterial or otherwise, to facilitate expression and/or, where desired, facilitate presentation of the expressed antigenic polypeptide on the bacterial cell surface (Cattozzo et al., J. Biotechnol 56, 191 (1997), Stocker and Newton, Int. Rev. Immunol. 11, 167 (1994), Stocker, Res. Microbiol. 141, 787 (1990), Newton et al., Science 244, 70 (1989), U.S. Pat. No. 6,130,082)). For example, Newton et al. (Res. Microbiol. 146, 203 (1995)) fused an HIV1 gp41 epitope, which is part of the gp160 protein, to a *Salmonella* flagellum gene in correct orientation and reading frame. The plasmid was placed in a flagellin-negative live-vaccine *Salmonella* strain, which then made a protein with the foreign HIV1 epitope sequence integrated into it. Mice immunized with live-vaccine of the recombinant *Salmonella* showed production of antibody with affinity for gp160.

The nucleotide sequence encoding an antigenic molecule may also be fused to with a nucleic acid, bacterial or otherwise, to facilitate presentation of the expressed antigenic polypeptide on the cell surface of the genetically engineered bacteria (Cattozzo et al., J. Biotechnol 56, 191 (1997), Stocker and Newton, Int. Rev. Immunol. 11, 167 (1994), Stocker, Res. Microbiol. 141, 787 (1990), Newton et al., Science 244, 70 (1989), U.S. Pat. No. 6,130,082)). For example, Newton et al. (Res. Microbiol. 146, 203 (1995)) fused an HIV1 gp41 epitope, which is part of the gp160 protein, to a *Salmonella* flagellum gene in correct orientation and reading frame. The plasmid was placed in a flagellin-negative live-vaccine *Salmonella* strain, which then made a protein with the foreign HIV1 epitope sequence integrated into it. Mice immunized with live-vaccine of the recombinant *Salmonella* showed production of antibody with affinity for gp160.

Immunopotency of the antigenic molecule expressed by the genetically engineered bacteria in an incapacitated, whole cell immunogenic preparation, can be determined by monitoring the immune response of test animals following immunization with the bacteria expressing the recombinant antigen. Test animals may include mice, guinea pigs, rabbits, chickens, chimpanzees and other primates, and eventually human subjects. Methods of introduction of the incapacitated recombinant bacteria may include oral, intradermal, intramuscular, intraperitoneal, intravenous, subcutaneous, intranasal or any other standard routes of immunizations.

The immune response of the test subjects can be analyzed by various approaches such as: (a) the reactivity of the resultant immune serum to the native antigen or a fragment thereof, or to the isolated naturally occurring organism (e.g., wild-type organism) from which the test antigenic molecule was derived, as assayed by known techniques, e.g., enzyme linked immunosorbant assay (ELISA), immunoblots, radioimmunoprecipitations, etc., (b) the reactivity of lymphocytes isolated from the immunized subject to the native antigen or fragment thereof, or the naturally occurring organism from which the test antigenic molecule was derived, as assayed by known techniques, e.g., blastogenic response assays, cytotoxicity assays, delayed type hypersensitivity, etc., (c) the ability of the immune serum to neutralize infectivity of the organism in vitro or the biologic activity of the native antigen, and (d) protection from disease and/or mitigation of infectious symptoms in immunized animals.

Use of Incapacitated Bacteria for Production of Antibodies

For the production of antibodies against an antigenic molecule expressed by bacteria, which bacteria may be genetically engineered to express a heterologous protein or to overexpress an endogenous protein, various host animals may be immunized by injection with an incapacitated whole cell immunogenic composition of the invention.

Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen. For the production of polyclonal antibodies, host animals such as those described above, may be immunized by injection with an incapacitated whole cell bacterial composition of the invention. The composition may be supplemented with adjuvants.

The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. Antibodies specific for an antigen, or fragment thereof, particularly for a recombinant antigenic molecule expressed by genetically engineered bacteria, can be selected for (e.g., partially purified) or purified by, e.g., affinity chromatography.

For example, a recombinantly expressed and purified (or partially purified) protein antigen is produced in genetically engineered bacteria as described herein, and covalently or non-covalently coupled to a solid support such as, for example, a chromatography column. The column may then be used to affinity purify antibodies specific for the proteins from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only about 30% (by dry weight) of contaminating antibodies directed against epitopes other than those on the desired protein or polypeptide of interest, and preferably at most about 20%, yet more preferably at most 10%, and most preferably at most about 5% (by dry weight) of the sample is contaminating antibodies. A purified antibody composition means that at least about 99% of the antibodies in the composition are directed against the desired antigenic protein or polypeptide.

Monoclonal antibodies, which are homogeneous populations of antibodies to a particular antigen, may be obtained by any technique that provides for the production of antibodies by, for example, continuous cell lines in culture. These include, but are not limited to, the hybridoma technique of Kohler and Milstein, (1975, Nature 256, 495-497; and U.S. Pat. No. 4,376,110), the human B-cell hybridoma technique (Kosbor et al., 1983, Immunology Today 4, 72; Cole et al., 1983, Proc. Natl. Acad. Sci. USA 80: 2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the desired mAb may be cultivated in vitro or in vivo. Production of high titers of mAbs in vivo makes this the presently preferred method of production.

Uses of Antibodies Directed Against Incapacitated Bacteria

The antibodies generated against the incapacitated whole cell immunogenic bacterial composition of the invention have potential uses in diagnostic immunoassays, passive immunotherapy, and generation of antiidiotypic antibodies. In one embodiment, the composition used to generate the antibodies comprises bacteria genetically engineered to express a heterologous protein or to overexpress an endogenous protein.

The generated antibodies may be isolated by standard techniques known in the art (e.g., immunoaffinity chromatography, centrifugation, precipitation, etc.) and used in diagnostic immunoassays to detect the presence of cancerous cells or viruses, bacteria, fungi or parasites of medical or veterinary importance in human or animal tissues, blood, serum, etc. The antibodies may also be used to monitor treatment and/or disease progression. Any immunoassay system known in the art, such as those listed herein, may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays and immunoelectrophoresis assays, etc., where such immunoassays are known in the art.

The vaccine preparations of the present invention can also be used to produce antibodies for use in passive immunotherapy, in which short-term protection of a host is achieved by the administration of pre-formed antibody directed against a heterologous organism.

The antibodies generated by the vaccine preparations of the present invention can also be used in the production of anti-idiotypic antibody. The antiidiotypic antibody can then in turn be used for immunization, in order to produce subpopulation of antibodies that bind the initial antigen of the pathogenic microorganism (Jerne, N. K., 1974, Ann. Immunol. (Paris) 125c:373; Jerne, N. K., et al., 1982, EMBO 1:234).

Formulations, Routes of Administration and Dosages

The immunogenic compositions of the invention can be formulated in any suitable manner. In general, the immunogenic compositions can be administered orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that the oral administration can require protection of digestion. This can be accomplished either by mixing or packaging the incapacitated bacterium in an appropriately resistant carrier such as a liposome. The preparations may also be provided in controlled release or slow-release forms for release and administration of the antigen preparations as a mixture or in serial fashion.

The immunogenic compositions of the invention are generally provided in combination with a pharmaceutically acceptable excipient. Various pharmaceutically acceptable excipients are well known in the art. As used herein, "pharmaceutically acceptable excipient" includes any material which, when combined with an active ingredient of a composition, allows the ingredient to retain biological activity and without causing disruptive reactions with the subject's immune system.

Exemplary pharmaceutically carriers include sterile aqueous of non-aqueous solutions, suspensions, and emulsions. Examples include, but are not limited to, any of the standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

A composition comprising an incapacitated bacterium of the invention may also be lyophilized using means well known in the art, for subsequent reconstitution and use according to the invention.

Also of interest are formulations for liposomal delivery, and formulations comprising microencapsulated whole cell bacterial vaccine. Compositions comprising such excipients are formulated by well known conventional methods (see, for example, Remington's Pharmaceutical Sciences, Chapter 43, 14th Ed., Mack Publishing Col, Easton Pa. 18042, USA).

In general, the pharmaceutical compositions can be prepared in various forms, such as granules, tablets, pills, suppositories, capsules (e.g. adapted for oral delivery), microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value.

The pharmaceutical composition can comprise other components in additional to the incapacitated bacterium. In addition, the pharmaceutical compositions may comprise more than one incapacitated bacteria, for example, two or more, three or more, five or more, or ten or more different incapacitated bacteria, where the different bacteria may be of the same or different serotypes, species, and the like. As noted above, the incapacitated bacteria can be administered in conjunction with other agents, such as a conventional antimicrobial agent (see table above). In some embodiments, it may be desirable to administer the incapacitated bacterium and antibiotic within the same formulation.

The compositions are administered to an animal that is at risk from acquiring a disease caused by the bacterial pathogen to prevent or at least partially arrest the development of disease and its complications. An amount adequate to accomplish this is defined as a "therapeutically effective dose." Amounts effective for therapeutic use will depend on, e.g., the antigen composition, the manner of administration, the weight and general state of health of the patient, and the judgment of the prescribing physician. Single or multiple doses of the compositions may be administered depending on the dosage and frequency required and tolerated by the patient, and route of administration.

Amounts for the immunization of the mixture generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration. The initial administration of the mixture can be followed by booster immunization of the same of different mixture, with at least one booster, more usually two boosters, being preferred.

The invention also contemplates that the immunogenic composition comprising an incapacitated bacteria can be used as a vaccine, and may include one or more strains of incapacitated bacteria.

The vaccines can be administered to any subject, generally a mammalian subject, that has or is susceptible to, infection by a bacterial pathogen. Subjects of particular interest include, but are not necessarily limited to, humans, and domesticated animals (e.g., livestock, pets, and the like) as well as animals held in captivity (e.g., in zoos or aquatic parks).

While the subject need not be immunologically naïve, the vaccines of the invention are typically administered to a subject that is immunologically naïve with respect to the particular bacterial pathogen. In a particular embodiment, the mammal is a primate (e.g., human) child about five years or younger, and preferably about two years old or younger. The vaccine of the invention can be administered as a single dose or, where desired or necessary, the initial dose can be followed by boosters at several days, several weeks, or several months or years following the initial dose. In general, administration to any mammal is preferably initiated prior to the first sign of disease symptoms, or at the first sign of possible or actual exposure to the bacterial pathogen.

EXAMPLES

The foregoing embodiments of the present invention are further described in the following examples. The following examples are put forth so as to provide those of ordinary skill in the art with a complete disclosure and description of how to make and use the present invention, and are not intended to limit the scope of what the inventors regard as their invention. The present invention is not limited by the specific examples, and variations will be apparent to those skilled in the art without departing from the scope of the present invention. In particular, any other heterologous protein, which will make the bacterial cell non-viable, can be substituted in the experiments of the following examples.

Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of an Expression Cassette with a Gene of Interest Using Different Promoters The pTrc, ptac and araBAD promoters were tested for their effect on expression of various recombinant proteins and also on viability of the cells expressing the recombinant proteins.

Gene Expression from Foreign Promoters.

Many proteins are expressed at low levels in vivo. To produce high levels of a protein, it is often useful to clone the gene downstream of a well-characterized, regulated promoter. Inducing transcription from the regulated promoter thus results in elevated expression of the downstream gene product. If the regulated promoter can be tightly down-regulated (e.g., turned off), this also provides a method of conditionally depleting the cell of a gene product. A variety of regulated promoters can be used for this purpose. A few examples are described below.

Ptac

The tac promoter/operator ($P_{TAC}$) is one of the most widely used expression systems. Ptac is a strong hybrid promoter composed of the −35 region of the trp promoter and the −10 region of the lacUV5 promoter/operator. Expression of Ptac is repressed by the LacI protein. The lacI^q allele is a promoter mutation that increases the intracellular concentration of LacI repressor, resulting in strong repression of $P_{TAC}$. Addition of the inducer—IPTG inactivates the LacI repressor. Thus, the amount of expression from $P_{TAC}$ is proportional to the concentration of IPTG added: low concentrations of IPTG result in relatively low expression from $P_{TAC}$ and high concentrations of IPTG result in high expression from $P_{TAC}$. By varying the IPTG concentration the amount of gene product cloned downstream from $P_{TAC}$ can be varied over several orders of magnitude.

Several potential problems must be considered when expressing a cloned gene product from $P_{TAC}$:

lacI^q should be cloned on the same plasmid as the regulated gene, because if lacI^q is on the chromosome or on another plasmid there may be insufficient LacI protein to fully repress the Ptac promoter in trans.

The cell viability should be measured at different concentrations of IPTG, because excessive overexpression of a DNA-binding protein may cause the protein to accumulate in inclusion bodies (Nilsson and Anderson, 1991) or inhibit cell growth.

Even when fully repressed, there is some residual expression from $P_{TAC}$. If this leaky expression causes problems, it may be necessary to clone the gene into an alternative expression vector that is more tightly repressed.

$P_{BAD}$.

The promoter for the *E. coli* arabinose operon ($P_{BAD}$ or $P_{ARA}$) is a useful alternative to $P_{TAC}$. When a gene is cloned behind the $P_{BAD}$ promoter, expression of the gene is controlled by the AraC activator. Expression from $P_{ARA}$ is induced to high levels on media containing arabinose. Moreover, expression from $P_{ARA}$ is tightly downregulated (e.g., shut off) when the bacterial host is grown on media containing glucose but lacking arabinose.

Like the arabinose operon, expression of the *E. coli* rhamnose operon is tightly regulated by an activator. Expression from the rhamnose promoter ($P_{RHA}$) is induced to high levels by the addition of rhamnose.

Phage Promoters.

Another approach to accomplish protein overexpression is to place a gene under the control of a regulated phage promoter. A gene may be cloned downstream of a tightly regulated phage promoter that is normally transcribed by the host's RNA polymerase. For example, expression of a gene cloned downstream of the lambda $P_L$ promoter can be regulated by the cI repressor. Using the temperature sensitive cI857 repressor allows control of gene expression by changing the growth temperature—at 30 C the cI857 repressor is functional and it turns off expression of the gene, but at 42 C the repressor is inactivated so expression of the gene ensues. Alternatively, the wild-type cI gene can be placed under the control of another regulated promoter such as the $P_{LAC}$ promoter, allowing inducible expression regulation by the addition of IPTG.

Alternatively, the gene may be cloned downstream of a phage promoter that relies on a phage encoded RNA polymerase. Many phage produce a specific RNA polymerase that recognizes a promoter sequence which is quite different from *E. coli* promoter sequences. Three phage-specific RNA polymerase/promoter systems that are commonly used in expression vectors include T7, SP6, and T3. In addition to recognizing unique promoters, these systems result in very high levels of transcription of the downstream gene. Such high-level transcription can be used overproduce a gene product operably linked to the phage promoter, but the expression is so high that it is often toxic to the host cell. To avoid potential toxicity the phage RNA polymerase is only induced when the overexpression is desired. For example, the phage RNA polymerase may be itself cloned behind a regulated promoter, or the polymerase may be introduced to the cell on a defective phage.

Example 2

Construction of an Expression Cassette Under T7 and Trc Promoter

This example describes cloning and expression of different types of heterologous proteins in the strong phage promoter system—T7 promoter. The genes are GFP from jellyfish *Aequorea Victoria*, NADH dehydrogenase of *Micrococcus luteus*, ndd gene of T4 bacteriophage etc.

GFP:

The GFP gene from jellyfish *Aequorea Victoria* in the plasmid pGLO (Biorad Laboratories, USA) is cloned at the EcoR1 site of the pRSET vector and the recombinants carrying the GFP gene are selected by restriction analysis. The plasmids are later used to transform BL21(DE3) cells for expression of the same monitored after IPTG induction. The BL21 has a potential advantage of being deficient in lon protease and also lacks ompT—an outer membrane protease that can degrade proteins. Bacteriophage DE3 is a lambda derivative that has the immunity region of the phage 21 and carries a DNA fragment containing the lacI gene, lacUV5 promoter, the beginning of the lacZ gene and the gene for T7 RNA polymerase. In DE3 cells, the only promoter known to direct transcription of the T7 RNA polymerase gene is the lacUV5 promoter, which is inducible by IPTG (Studier et al 1990). The data obtained (FIG. 1) indicates that there is an approximately 98% loss in viability of cells expressing rGFP.

NADH Dehydrogenase:

The PCR amplification of the NADH dehyfdrogenase gene is done from the genomic DNA of *Micrococcus luteus* and the purified PCR product is digested with Nde1/HindIII (sites incorporated in the oligonucleotides) and cloned into ampicillin resistant pET vector in the same sites in the MCS region. The expression of the protein is monitored in BL21(DE3) cells after IPTG induction and the viability of the cells expressing the foreign protein is monitored by plating. [From FIG. 2 it is clear that although there is no effect on the growth rate of cells expressing recombinant NADH dehydrogenase, there is almost 100% death of cells expressing this protein.

To examine the effect of vector alone in the cells carrying them after IPTG induction, BL21(DE3) cells carrying the vector-pRSETA was induced with IPTG as described above. The results indicated (FIG. 3) that there is drastic loss of viability in cells carrying vector alone which indicates that T7 RNA polymerase may be the causative agent for the viability loss.

In another embodiment of the invention, the recombinant protein expressed to incapacitate the bacterial host is a phage protein. Below two different T4 phage proteins—holin and lysin were expressed from an *E. coli* Trc promoter—pTrc99A (Amann et al 1988) and the effect of expression of these proteins on cell viability studied.

Holin:

Holin gene from T4 phage DNA is PCR amplified using holin specific primers and then cloned into EcoR1/HindIII in pET vectors and the same gene is subcloned into similar sites in pTrc promoter based vector-pTrc99A. The expression of the T4 holin gene is monitored in DH5α cells and the effect of the following on viability status of the cells is examined. Several pathogenic *E. coli* cells are taken and transformed with the same plasmid carrying holin gene in pTrc vector and the viability checked upon IPTG induction. Results indicated that there is severe loss of viability of the cells expressing holin (FIGS. 4 to 9).

Lysozyme:

The T4 phage lysozyme gene is PCR amplified from the T4 phage lysate and cloned as BamH1/HindIII in pTrc99A vector in similar sites. The recombinants carrying the inserts are identified by PCR for T4 lysin using lysin specific primers and then the induction is carried out in DH5α cells with 2 mM IPTG for 4 hours at 37 deg C. and viability checked every hour. Suitable vector controls are also run for comparison. The results indicated (FIG. 10 and FIG. 11) significant loss of viability of the cells expressing lysozyme while there is no loss in case of vector induced under similar conditions.

Other Gene Products of Interest for Use in Production of Incapacitated Bacterial Host Cells T4 ndd Gene:

The ndd gene is PCR amplified using appropriate oligonucleotides from the T4 phage DNA and after digestion with Nde1/HindIII is cloned into the ampicillin resistant pET vector into the Nde1/HindIII sites. The recombinants carrying the ndd insert are screened by PCR for ndd gene by ndd gene specific primers and the expression of the ndd gene product is monitored in BL21(DE3) cells upon IPTG induction. The viability of the cells expressing the above gene product is assessed by plating on suitable L bagar plates with appropriate antibiotics.

T7 RNA Polymerase:

Bacteriophage T7 RNA polymerase coding sequence of 2651 base pairs is PCR amplified from T7 phage DNA and then cloned into suitable sites of expression vectors with pTac/pBAD/pTrc promoter system. The effect of the expression of the above protein on viability of the cells is monitored.

Endotoxin Binding Protein:

The bactericidal permeability binding protein (rBP21) is PCR amplified from hepatic liver cDNA and then the N terminal and the C terminal portions is separately cloned into pET vector. The sCD14 is also PCR amplified and cloned into suitable expression vectors. The effect of expression of all these proteins on viability of the bacterial cells is examined.

Hosts Types:

Similar experiments are carried out with vectors compatible in several other hosts like *Pseudomonas, Staphylococcus, Klebsiella, Bacillus, Proteus* etc for establishing the loss of viability upon induction of a foreign protein.

References Cited in Examples:

The following references are of interest in the practice of the examples above:

Amann E, Brosius J, Ptashne M. 1983. Vectors bearing a hybrid trp-lac promoter useful for regulated expression of cloned genes in *Escherichia coli*. Gene 25: 167-178.

Guzman L M, Belin D, Carson M J, Beckwith J. 1992. Tight regulation, modulation, and high-level expression by vectors containing the arabinose PBAD promoter. J Bacteriol. 177: 4121-4130.

Haldimann, A., L. Daniels, B. Wanner 1998. Use of new methods for construction of tightly regulated arabinose and rhamnose promoter fusions in studies of the *Escherichia coli* phosphate regulon. J. Bacteriol. 180: 1277-1286.

Studier, F., and B. Moffatt. 1986. Use of bacteriophage T7 RNA polymerase to direct selective high-level expression of cloned genes. J. Mol. Biol. 189: 113-130.

Studier W, Rosenberg A H, J J Dunn and Dubendroff J W (1990) Methods in Enzymology, 185, 60-63

Amann E, Ochs B and Abel Karl-Josef 1988. Tightly regulated tac promoter vectors useful for the expression of unfused and fused proteins in *E. coli*. Gene, 69, 301-315

Example 3

In Vivo Vaccination

An animal model is used to demonstrate that bacteria incapacitated by the present invention are capable of inducing an immune response in the host animal. The animal is vaccinated with an incapacitated immunogen prepared, e.g., as described above. After a sufficient period of time to allow the production of an immune response, the animals are challenged with live form of the bacteria. The response of vaccinated animals is compared with control animals vaccinated with a control composition.

For example, whole cell immunogen is prepared as described. Animals are vaccinated with 3 appropriate doses of the incapacitated bacteria at appropriate intervals, e.g., 2-3 weeks between vaccinations. The vaccines are formulated with adjuvants and appropriate carriers and excipients. Antibody titers may be monitored compared to mock immunizations, e.g., immunizations with adjuvant lacking the incapacitated bacteria, and the immune responses may be characterized.

Beyond antibody titer, the effectivenss of the immune response can also be tested. For example, the animals may be challenged with live bacteria. The effectiveness of response may be evaluated by clearance of the bacteria, or by decrease in pathogenicity of the bacteria. Survival rates, e.g., after challenge with a lethal dose of bacteria, may be evaluated.

Swiss Albino mice are immunized via intraperitoneal route, using pathogenic *E. coli* cells (MTCC#443) that are killed with lysis-deficient phage (incapacitated whole cells) generated by one of the means described. Three doses of the $10^4$ killed cells are administered at four-day intervals. Four days after the last immunization, the mice are challenged with an $LD_{80}$ dose of live pathogenic *E. coli* (MTCC#443) cells. For controls, heat killed/formaldehyde treated cells are included. The mice are bled and serum collected for analysis for presence of anti-*E. coli* antibodies. In all the ELISA assays the pre-immune sera are used as blank.

The experimental details and results of such an example of in vivo vaccination are set out in the tables below.

TABLE III

Post-Immunization and challenge Results

| Test group | Mortality after immunization | Mortality after challenge | % survival/ protection |
|---|---|---|---|
| Vehicle control Saline | — | 4/10 | 60% |
| +ve Control 1 Heat Killed cells | Nil | 1/10 | 90% |
| +ve Control 2 Formaldehyde - killed cells | Nil | 1/10 | 90% |
| Test 1 Holin-expressed killed cells | Nil | 1/10 | 90% |
| Test 2 Over exp. T7 RNA POL killed cells | Nil | 2/10 | 80% |
| +ve Serum control Heat Killed cells | Nil | Not challenged | 100% |

TABLE IV

Serum analysis for presence of anti-*E. coli* antibodies - ELISA results

| Test Group | No. of mice surviving challenge | No. of samples analyzed * | No. of samples showing anti-*E. coli* antibody | % animals showing immune response |
|---|---|---|---|---|
| Heat Killed cells Unchallenged +ve serum control | 10/10 | 4 | 3/4 | 75% |
| Saline Vehicle control | 6/10 | 2 | 2/2 | 100% |
| Heat Killed cells +ve control | 9/10 | 5 | 3/5 | 60% |
| Formaldehyde- killed cells +ve control | 9/10 | 6 | 6/6 | 100% |
| Holin-expressed killed cells | 9/10 | 6 | 5/6 | 83% |
| Over exp. T7 RNA POL killed cells | 8/10 | 6 | 5/6 | 83% |

* serum was collected from mice (randomly selected) prior to immunization to confirm absence of antibodies to *E. coli*

TABLE II

Experimental details

| Test Groups | Category | No. of animals | Immunization (i.p.) DAYS 1, 5, 9 | Challenge (i.p.) DAY 13 |
|---|---|---|---|---|
| 1 | Vehicle control Saline | 5 + 5* | Yes | Yes |
| 2 | Heat Killed cells | 5 + 5 | Yes | Yes |
| 3 | Over exp. T7 RNA POL killed cells | 5 + 5 | Yes | Yes |
| 4 | Live cells | 5 + 5 | Yes | Yes |
| 5 | Formaldehyde- killed | 5 + 5 | Yes | Yes |
| 6 | Holin-expressed killed cells | 5 + 5 | Yes | Yes |
| 7 | Thymol killed cells | 5 + 5 | Yes | Yes |
| 8 | Heat Killed cells | 5 + 5 | Yes (+ve serum collection) | NO |

*indicates 5 animals in each group mentioned in the adjacent columns

That which is claimed is:

1. A method of immunizing a subject against a bacterial pathogen, the method comprising:

administering to the subject an incapacitated immunogenic bacterial composition comprising the bacterial pathogen carrying an expression vector comprising a recombinant promoter operably linked to a polynucleotide encoding a gene product, wherein the recombinant promoter is a bacteriophage promoter, and wherein the bacterial pathogen is recombinantly modified to express a bacteriophage RNA polymerase for transcription from the bacteriophage promoter, wherein expression of the gene product is at a level sufficient to render the bacterial pathogen incapacitated, thereby producing said incapacitated immunogenic bacterial composition, wherein administration of said incapacitated immunogenic bacterial composition elicits an immune response to an antigen on the bacterial pathogen, thereby immunizing the subject against the bacterial pathogen, and wherein
- (i) the bacteriophage promoter is a T7 bacteriophage promoter and the bacteriophage RNA polymerase is T7 RNA polymerase,
- (ii) the bacteriophage promoter is a SP6 bacteriophage promoter and the bacteriophage RNA polymerase is SP6 RNA polymerase,
- (iii) the bacteriophage promoter is a T3 bacteriophage promoter and the bacteriophage RNA polymerase is T3 RNA polymerase, or
- (iv) the bacteriophage promoter is a T7 bacteriophage promoter and the bacteriophage RNA polymerase is T7 RNA polymerase.

2. The method of claim 1, wherein the bacterial pathogen is of a genus selected from the group consisting of *Bordetella*, Mycobacteria, Staphylococci, *Vibrio, Enterobacter, Enterococcus, Escherichia, Haemophilus, Neisseria, Pseudomonas, Shigella, Serratia, Salmonella, Streptococcus, Klebsiella* and *Yersinia*.

3. The method of claim 1, wherein the expression cassette is on a plasmid.

4. The method of claim 1, wherein the bacterial pathogen is *Escherichia coli* or *Staphylococcus aureus*.

* * * * *